(12) United States Patent
Mitchell et al.

(10) Patent No.: US 10,849,927 B2
(45) Date of Patent: Dec. 1, 2020

(54) POLYSACCHARIDE-POLYAMINE COPOLYMERS FOR REMOVAL OF PHOSPHATE

(71) Applicant: HOWARD UNIVERSITY, Washington, DC (US)

(72) Inventors: James W. Mitchell, Durham, NC (US); Dazhi Yang, Gaithersburg, MD (US)

(73) Assignee: HOWARD UNIVERSITY, Washington, DC (US)

(*) Notice: Subject to any disclaimer, the term of this patent is extended or adjusted under 35 U.S.C. 154(b) by 344 days.

(21) Appl. No.: 15/560,131

(22) PCT Filed: Mar. 18, 2016

(86) PCT No.: PCT/US2016/023237
§ 371 (c)(1),
(2) Date: Sep. 20, 2017

(87) PCT Pub. No.: WO2016/154043
PCT Pub. Date: Sep. 29, 2016

(65) Prior Publication Data
US 2018/0099007 A1    Apr. 12, 2018

Related U.S. Application Data

(60) Provisional application No. 62/136,220, filed on Mar. 20, 2015.

(51) Int. Cl.
*A61K 31/785* (2006.01)
*A61K 31/738* (2006.01)
(Continued)

(52) U.S. Cl.
CPC ............ *A61K 31/785* (2013.01); *A61K 9/14* (2013.01); *A61K 31/738* (2013.01); *A61P 7/08* (2018.01);
(Continued)

(58) Field of Classification Search
None
See application file for complete search history.

(56) References Cited

U.S. PATENT DOCUMENTS 4,663,163 A * 5/1987 Hou .................. B01J 20/28028
210/198.2
5,340,731 A * 8/1994 Kilburn .................. A61K 39/39
435/177
(Continued)

FOREIGN PATENT DOCUMENTS

WO         2014/029888 A2     2/2014

OTHER PUBLICATIONS

Kuga et al. "Polyallylamine-grafted cellulose gel as high-capacity anion-exchanger", Journal of Chromatography A, 946, 2002, pp. 283-289. (Year: 2002).*

(Continued)

*Primary Examiner* — Carlos A Azpuru
*Assistant Examiner* — Casey S Hagopian
(74) *Attorney, Agent, or Firm* — Sughrue Mion, PLLC

(57) ABSTRACT

Covalently cross-linked copolymers are described herein. More specifically, polysaccharide-polyamine copolymeric matrices or structures and cationic copolymeric matrices are described herein. The polysaccharide-polyamine copolymers, when protonated, can form cationic copolymeric matrices having exceptionally high densities of cationic sites. In one form, the covalently cross-linked copolymers provide a three-dimensional structure, especially when hydrated.

17 Claims, 10 Drawing Sheets

(51) Int. Cl.
| | |
|---|---|
| *B01J 20/26* | (2006.01) |
| *B01J 20/28* | (2006.01) |
| *B01J 20/30* | (2006.01) |
| *C08B 15/06* | (2006.01) |
| *C08G 81/00* | (2006.01) |
| *C08G 83/00* | (2006.01) |
| *C08J 9/16* | (2006.01) |
| *A61K 9/14* | (2006.01) |
| *C08F 251/02* | (2006.01) |
| *C08G 73/02* | (2006.01) |
| *C08L 1/08* | (2006.01) |
| *C08L 3/20* | (2006.01) |
| *C08L 5/02* | (2006.01) |
| *C08L 5/08* | (2006.01) |
| *C08G 101/00* | (2006.01) |
| *A61P 7/08* | (2006.01) |

(52) U.S. Cl.
CPC ........... *B01J 20/264* (2013.01); *B01J 20/267* (2013.01); *B01J 20/28004* (2013.01); *B01J 20/28078* (2013.01); *B01J 20/28085* (2013.01); *B01J 20/3085* (2013.01); *C08B 15/06* (2013.01); *C08F 251/02* (2013.01); *C08G 73/0206* (2013.01); *C08G 81/00* (2013.01); *C08G 83/002* (2013.01); *C08J 9/16* (2013.01); *C08L 1/08* (2013.01); *C08L 3/20* (2013.01); *C08L 5/02* (2013.01); *C08L 5/08* (2013.01); *C08G 2101/00* (2013.01); *C08G 2210/00* (2013.01); *C08J 2205/022* (2013.01); *C08J 2207/10* (2013.01); *C08J 2387/00* (2013.01)

(56) References Cited

U.S. PATENT DOCUMENTS

| | | | |
|---|---|---|---|
| 5,496,545 | A | 3/1996 | Holmes-Farley et al. |
| 5,766,908 | A | 6/1998 | Klein et al. |
| 8,163,799 | B2 | 4/2012 | Dhal et al. |
| 8,889,738 | B2 | 11/2014 | Dhal et al. |
| 8,900,560 | B2 | 12/2014 | Dhal et al. |
| 2004/0010137 | A1 | 1/2004 | Jaschinski et al. |
| 2005/0002893 | A1* | 1/2005 | Goldmann ............ A61L 24/043 424/70.27 |
| 2008/0317861 | A1 | 12/2008 | Guan |
| 2010/0272804 | A1 | 10/2010 | Lu |
| 2012/0237470 | A1 | 9/2012 | Dhal et al. |

OTHER PUBLICATIONS

Patent Cooperation Treaty, International Search Report and Written Opinion of the International Searching Authority or International Application No. PCT/US2016/023237 dated Jun. 10, 2016, 17 pages.

Kuga, Shigenori, and Kim, Ung-Jin, "Polyallylamine-grafted cellulose gel as high-capacity anion-exchanger," Journal of Chromatography A, 946, 2002, pp. 283-289.

Patent Cooperation Treaty, International Search Report and Written Opinion of the International Searching Authority for International Application No. PCT/US2016/023248 dated May 31, 2016, 13 pages.

* cited by examiner to FIG. 1B

POLYSACCHARIDE-POLYAMINE COPOLYMERS FOR REMOVAL OF PHOSPHATE

CROSS-REFERENCE TO RELATED APPLICATIONS

This application is a U.S. national phase application filed under 35 U.S.C. § 371 of International Application Number PCT/US2016/023237, filed Mar. 18, 2016, designating the United States, which claims benefit of the U.S. Provisional Application No. 62/136,220, filed Mar. 20, 2015.

FIELD

The present application is generally directed to protonatable copolymers and, more specifically, covalently cross-linked copolymers, such as in the form of a gel or powder, their use, and manufacture.

BACKGROUND

In the United States, 5-7% of the total population have moderate Chronic Kidney Disease (CKD) and similar incident rates are reported from several other countries. Without efficient treatment, many moderate CKD patients progress to CKD stage 5, end-stage renal disease (ESRD). The epidemiology studies show that the cases of ESRD are continually increasing. At the end of 2011, there were 615,899 patients receiving treatment for end-stage renal disease (ESRD) in United States. There were 115,643 new cases of ESRD reported in 2011, a 3.2 percent increase from 2010 (United States Renal Data System 2013).

The kidney plays a key role in maintaining human phosphorus homeostasis through urinary phosphate excretion. In the later stages (4 and 5) of CKD, the glomerular filtration rate (GFR) falls below 25 to 40 mL/min. The decrease of glomerular filtration (GFR) results in the reduction of urinary excretion of phosphate. The buildup of the phosphate leads to the abnormal elevation of serum phosphate, called hyperphosphatemia. The progressively increasing hyperphosphatemia significantly associates with the increase of mortality rate through its debilitating complications including secondary hyperparathyroidism, renal osteodystrophy, cardiovascular calcification, and calciphylaxis in the dialysis patients. Extensive studies show that patients with very high serum phosphate levels (>3.6 mM) had 2.5-fold mortality rates as compared with patients with much lower phosphate levels (1.3 to 1.6 mM).

Phosphate removal through dialysis is very limited in ESRD patients, since most of the inorganic phosphorous is intracellular. Therefore, dietary phosphate restriction and oral phosphate binders are required to limit phosphate absorption within the digestion system. By binding phosphate in the GI tract, phosphate binders make the dietary phosphorus or phosphate unavailable for absorption. There are two types of phosphate binders, calcium-containing agents and non-calcium-containing agents. The calcium-containing phosphate binders, such as calcium acetate (PhosLo, Eliphos) and calcium carbonate (Turns, Os-Cal, Caltrate), are the most commonly used phosphate binders. Although they are able to reduce the absorption of phosphorus, application of these calcium containing agents may significantly contribute to calcium loading and increase the chance of hypercalcemia in hemodialysis patients. Under hyperphosphatemia conditions, elevation of calcium loading will increase the calcium×phosphorus (Ca×P) product. Patients with elevated Ca×P product values are facing significantly higher risk of death associated with cardiovascular calcification and its complications.

There are three available non-calcium phosphate binders including lanthanum carbonate (Fosrenol), Sevelamer (Renagel, Renvela) and Kiklin (Bixalomer). Lanthanum is an inorganic element and forms insoluble lanthanum phosphate through binding with phosphate. Even lanthanum is very poorly absorbed through oral administration. But the elimination of absorbed lanthanum is also very slow. Thus, lanthanum deposition was found in bone in low concentrations after one year treatment. Although its long-term effects on bone are uncertain, lanthanum is not recommended in pediatric patients.

Additionally, lanthanum has noticeable side effects such as myalgia, muscular cramping, and peripheral edema. Lanthanum recipients show the highest withdrawal rate (14%) owing to adverse events comparing with 4% of those who received other binders. Sevelamer is a non-inorganic material in the form of a non-absorbable hydrogel of a cationic polymer. Chemically, Sevelamer is poly(allylamine) hydrochloride or carbonate cross-linked with epichlorohydrin. It is able to more sufficiently reduce serum phosphorus levels than calcium-based phosphate binders and lanthanum carbonate with less adverse reaction, especially hypercalcemia and metal accumulation. Though Sevelamer is able to sufficiently remove phosphate with fewer side effects, there are two noticeable limitations. First, the epichlorohydrin used for cross-linking the poly(allylamine) to synthesize Sevelamer is known as a carcinogenic and potentially genotoxic reagent. As a hydrogel with poor solubility, it is very hard to remove epichlorohydrin from Sevelamer. Prolonged rinsing is required to ensure epichlorohydrin levels of the final product complies with the regulatory requirement of European Medicines Agency (EMEA), International Conference on Harmonization (ICH) and Food and Drug Administration (FDA) (http://www.epa.gov/ttn/atw/hlthef/epichlor.html) (http://www.epa.gov/iris/subst/OOSO.htm). Secondly, the significantly high cost of poly(allylamine), the monomer of Sevelamer, made it a higher economic burden on the health care systems in developed countries and less affordable for the majority of CKD patients of developing countries. Bixalomer, a newly developed nonmetallic anion exchange resin, has the same efficiency on reducing serum phosphorus levels with less adverse reaction. However epichlorohydrin is still applied as a cross linking reagent for Bixalomer (http://pubchem.ncbi.nlm.nih.gov/summary/summary.cgi?sid-124490326&viewopt=PubChe m). Furthermore, the costs of Bixalomer remain substantially high.

SUMMARY

Covalently cross-linked copolymers are described herein. More specifically, polysaccharide-polyamine co-polymeric matrices or structures and cationic copolymeric matrices are described herein. The polysaccharide-polyamine copolymers, when protonated, can form cationic copolymeric matrices having exceptionally high densities of cationic sites. In one form, the cross-linked copolymers provide a three dimensional structure, especially when hydrated.

According to one form, the polysaccharide-polyamine polymeric matrices are the result of the reaction of two pre-existing polymers or large molecules. In accordance with one form, the polysaccharide-polyamine copolymers may be considered di-block copolymers. In one form, the polysaccharide-polyamine copolymers are a reaction product of polysaccharide-polyamine copolymers having 2,3 di-aldehyde moieties and amine polymers having polyfunctional amino functionality reactive with the aldehyde moieties. The latter reaction product includes particulate covalently cross-linked copolymers which are the polysaccharide-polyamine copolymers, such as cellulose-polyamine copolymers, having a three dimensional structure. The amino functionality provides the cationic copolymers with cationic functionality when the amino functionality in the polysaccharide-polyamine copolymeric material is protonated.

In one aspect, the polysaccharide polymers are selected from the group consisting of selectively oxidized cellulose, selectively oxidized starch, selectively oxidized chitosan, selectively oxidized dextran, selectively oxidized glycogen, selectively oxidized chitin, and mixtures thereof. Selectively oxidized refers to having the hydroxyls at the C2 and C3 positions from di-aldehyde oxidized with concomitant cleavage of the C2-C3 bond where the oxidation will not produce more carboxyl groups than aldehyde groups and will not cleavage the polysaccharide chain.

In a very important aspect the polysaccharide polymers are cellulosic polymers selected from the group consisting of selectively oxidized cellulose, selectively oxidized chitosan, and mixtures thereof. As used herein, selectively oxidized cellulose, selectively oxidized starch, selectively oxidized chitosan, selectively oxidized dextran, selectively oxidized glycogen, selectively oxidized chitin means oxidized to the aldehyde. The latter selectively oxidized cellulose, selectively oxidized chitosan are important because they contain a β-1,4 glycosidic bond which cannot be digested by humans. The polymers such as cellulose, starch, chitosan, dextran, glycogen, and chitin are oxidized in an amount effective to provide the aldehyde moieties which are reactive with the amine polymers to permit the water soluble oxidized cellulosic polymers to react with the polyamine functional polymers which in turn provide the cross-linked matrix or three dimensional structure having amino functionality which can be protonated.

The latter polysaccharide-polyamine copolymer matrices and cationic matrices are not digestible by humans. The polysaccharide-polyamine copolymeric matrices are three dimensional covalently cross-linked matrices of polysaccharide polymers linked together with the polyamine polymers, especially when hydrated. This three dimensional structure of covalently cross-linked copolymers are in a particulate form, the particulates having a size in the range from about 100 μm to about 10 mm. The dehydrated form of the polysaccharide-polyamine copolymers or copolymeric matrices does not carry any permanent charges. These copolymers contain abundant amine groups and non-detectable amounts (<0.1 μmoles/g) of imino groups. Amines and imines are classified as weak bases with pKa value in the range of from 9 to 11. When exposed to an aqueous environment with a pH lower than 9.0, the polysaccharide-polyamine copolymers or copolymeric matrices will be rehydrated, swelled, protonated and formed a cationic polymeric matrix.

The polysaccharide-polyamine copolymeric particles and cationic copolymeric particles have structures that are porous. Both the gels and the copolymeric particles comprise a homogeneous combination of the reaction product of the polysaccharide-derived polymers (with the aldehyde functionality) and polyamino polymeric cross-linkers as compared to a cellulosic shell encasing polymeric amino or amido compounds reacted with carboxylic acids. When in particulate form, the pores in the polysaccharide-polyamine copolymeric matrix and/or protonated polysaccharide-polyamine copolymeric matrix range in size of less than 50 μm, and in an important aspect from about hundreds of nanometer to about 50 μm.

In one aspect, polysaccharide-polyamine polymer structures are provided having high densities of substituted amines, e.g., the primary, secondary, or tertiary amine. According to one aspect, gels and polymeric particles may be provided from the compositions herein. The gels and copolymeric particles may comprise a three-dimensional densely interlocked network of backbone strands, such as cellulosic strands, covalently cross-linked by the copolymer regions of the amino polymer. This intricately bonded three-dimensional net matrix of cellulosic polymers and polyamino polymeric cross-linkers are contrasted with a cellulosic shell encasing polymeric amino or amido compounds reacted with carboxylic acids.

The polysaccharide polymers, such as cellulose, starch, chitosan, dextran, glycogen, and chitin, are oxidized in an amount effective to provide the 2,3 aldehyde moiety which is reactive with the amino polymers to permit the oxidized polymers to react with polyamino functional polymers which in turn provide the cross-linked structure having a nitrogen content of at least 12.5 weight percent, based upon the weight of the polysaccharide copolymer. The amino polymers cross-link the polysaccharide polymers, such as water soluble cellulosic polymers (having the di-aldehyde moieties) to provide the three-dimensional structure of polysaccharide-derived "backbones" where multiple polysaccharide chains are linked with multiple chains of the amino polymers. These polysaccharide polymers are pre-existing polymers which are "blocks" or "backbones" linked together by pre-existing amino polymers which also are discrete amino blocks. In one form, the polysaccharide-polyamine copolymers may be considered to be di-block copolymers. The linked backbones are bonded together as the covalently cross-linking products of the amine polymers (which form cross-linking blocks) and the selectively oxidized polysaccharide to provide cross-linked block copolymer and copolymeric matrices with high percent of amine content which may be protonated.

The latter polysaccharide-polyamine copolymers which form the particulate polysaccharide-polyamine structures may be protonated (in the human body, or by controlling the pH) into cationic polymeric structures with extremely high charge densities. For example, the latter cross-linked polysaccharide-polyamine copolymers which form the copolymeric matrices may be protonated, when exposed to an aqueous environment with a pH lower than 9.0. The polysaccharide-polyamine copolymer may be protonated in an amount effective to provide the cationic copolymeric matrices with a nitrogen content of at least 12.5 wt. % based upon the weight of the cationic copolymers. Further as previously noted, the resulting polysaccharide-polyamine copolymers are insoluble in water.

The polysaccharide-polyamine copolymers have substituted ammonium ion, which are positively charged or protonated substituted amines, e.g., $RNH_{3+}$, $R_2NH_{2+}$ and $R_3NH_+$ formed by the protonation of substituted amines, e.g., $RNH_2$, $R_2NH$ and $R_3N$. The polymeric matrices are positively charged or protonated at the amine positions indicated previously to form all of the substituted ammonium ion including the quaternary ammonium cation ($HNR3+$), where one or more hydrogen atoms may be replaced by organic radical groups (indicated by R). The high charge density is effective to bind at least about 2.58±0.43 mmol/g under 6.25 mM phosphate condition at pH 7.0. In effect, the cationic matrices act as scavengers to remove phosphate from mammals including humans.

In one aspect the amino polymers are dendrimers which are macromolecular amines that have a core or center which includes amine groups and branches that include these functional groups which may be formed through a series of iterative reactions starting with the functional groups at the core or center to provide a highly branched amine polymer. In one aspect, the dendrimer molecule may be round or substantially round or have a three-dimensional morphology which is spherical or has an outer perimeter which is curvilinear or bounded by curved lines. In an important aspect the dendrimer has an nitrogen content of at least 30 wt. % based upon the weight of the dendrimer which is effective to provide the polysaccharide-polyamine copolymeric material when protonated (which results in the cationic polymer matrix) with a nitrogen content of at least about 12.3 wt. %, and preferably in the range of 10-30 wt. %, based upon the weight of the cationic material. In another form, branched forms of the amino polymers may also be used alone or in combination with the dendrimeric forms.

The amine polymers include branched amine polymers, dendritic amino polymers, and the amino polymers generally described in U.S. Pat. No. 8,889,738 and WO 2014/029888 which are incorporated as if fully rewritten herein. In a very important embodiment, the amino polymers which provide the polysaccharide-polyamine copolymeric materials with amino functionality (and cationic functionality when protonated after cross-linking the polysaccharide polymers) are selected from the group consisting of polyethylenimine (PEI), poly(allylamine), polypropylenimine and mixtures thereof. The polyethylenimine, poly(allylamine), polypropylenime can be in their branched or dendrimeric form, such as found in the attached figures.

Methods for making the polysaccharide-polyamine copolymeric materials and the cationic copolymeric materials also are described herein. The method includes oxidizing polysaccharide polymers, then reacting the polysaccharide-derived polymers having 2,3 di-aldehyde moieties as described above with amino polymers to provide the polysaccharide-polyamine copolymeric materials. If a primary amine of amino polymer is reacted with aldehyde moieties of oxidized polysaccharide and an imine is the reaction product, the imine converted to a substituted secondary amine through reducing the carbon nitrogen double bond to a single bond via a reduction reaction such as a hydride reduction reaction.

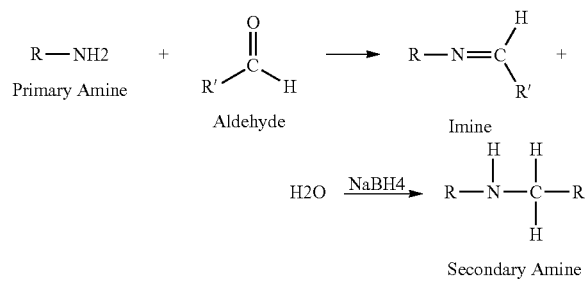

The oxidation level of polysaccharide, amine percent of the amino polymer, the size of the amino polymer, and the ratio of oxidized polysaccharide to the amino polymer all affect the formation of the polysaccharide-polyamine copolymer and copolymeric matrices. In an important aspect the selective oxidized polysaccharide have oxidized glucose unit of at least 50% (wt. %), and preferably above 80%. For PLA, the Mw is in the range of from about 17,000 to about 900,000 and the Mw for PEI is in the range of from about 25,000 to about 750,000 and the Mn is in the range of from about 60,000 to about 750,000. For PEI and/or Poly(allylamine) (PLA) having Mw of 15,000 to 25,000 Da, the ratio of the polysaccharide polymer to the latter amino polymers is in the range of about 1:1 to about 1:8. When the Mw of the amino polymer is in the range of 65,000 to 750,000 Da, the ratio of polysaccharide polymer to amino polymer is in the range of about 1:5 to about 1:20.

Methods of removal of phosphate compounds from the human body and other mammalian bodies also are described herein. The methods include the oral administration of the polysaccharide-polyamine copolymeric material and/or cationic copolymeric material having exceptionally high densities of cationic sites. The in vitro phosphate binding capacity assay show the polysaccharide-polyamine copolymer has similar phosphate binding capacity as Sevelamer. The phosphate binding capacity of these materials at an equivalent nitrogen amount (unit weight) under the same conditions (including pH) exceeds that of cellulose cross-linked by epichlorohydrin or poly(allylamine), which have higher percent of cationic content and higher composition cost.

A biocompatible cationic polymer is produced to sustain a high positive charge density resulting in strong bonding of polyvalent anions including phosphate, negatively charged peptides, and anions of metals, etc. The high purity good manufacturing practice (GMP) grade material can be formulated into a drug for treatment of hyperphosphatemia, induced by chronic kidney diseases.

In another aspect, the polysaccharide-polyamine copolymers also may be used for removing or scavenging other anionic inorganic and/or organic solutes or particles, such as carbonate, bicarbonate, polypeptides, bile acids, and oxalate containing compounds or ions. In one form, this may be performed on water, wastewater, and the like, as well as for removal from the human body.

A low cost commodity form of the cationic material derived from cellulose containing natural raw materials such as wood shavings, straw, agricultural byproducts, etc. can be applied for removal of environmental pollutants from industrial waste water and agricultural runoff water. The strong ion association property permits the complexion and immobilization of metal anions serving as environmental pollutants, as well as phosphate and nitrate, key eutrophication pollutants.

These and other aspects may be understood more readily from the following description and the appended drawings.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

DETAILED DESCRIPTION

Figures 1, 1A, 1B:
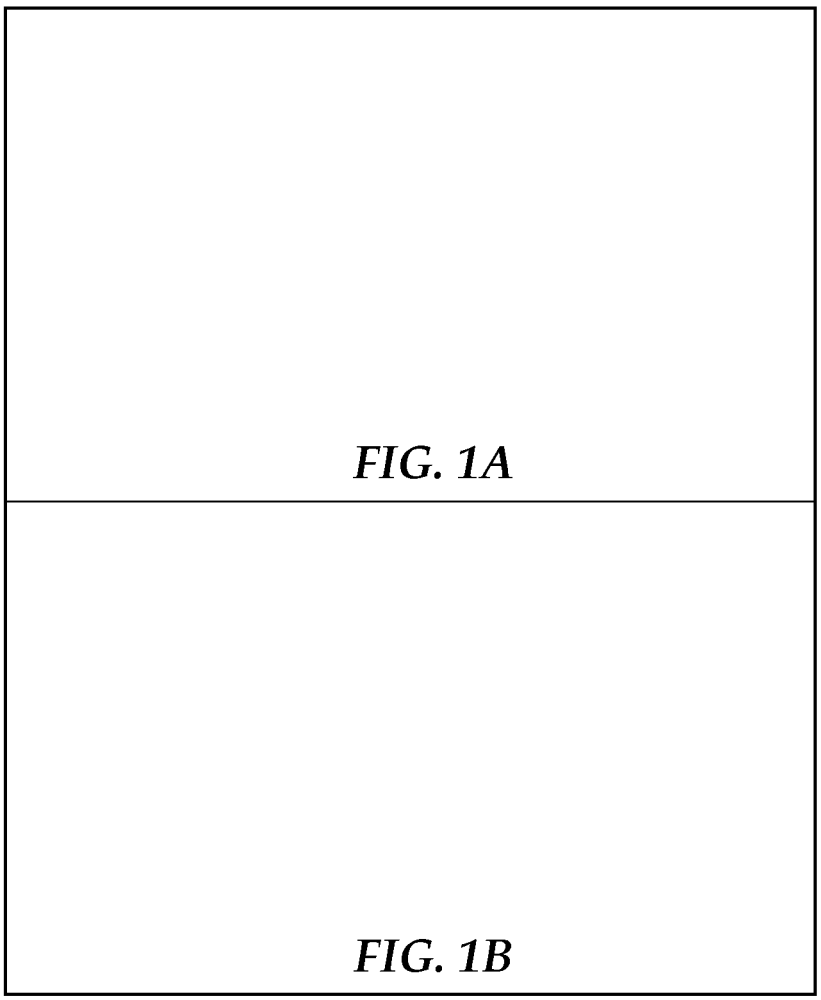
FIG. 1 is a diagram representing the combination of FIGS. 1A and 1B for a general chemical structure for one exemplary form of a covalently cross-linked copolymer, such as an polysaccharide-polyamine copolymer.
FIGS. 1A and 1B are partial chemical structures for one exemplary form of a covalently cross-linked copolymer, such as an polysaccharide-polyamine copolymer, which would be combined as shown in FIG. 1
Figure 1A:
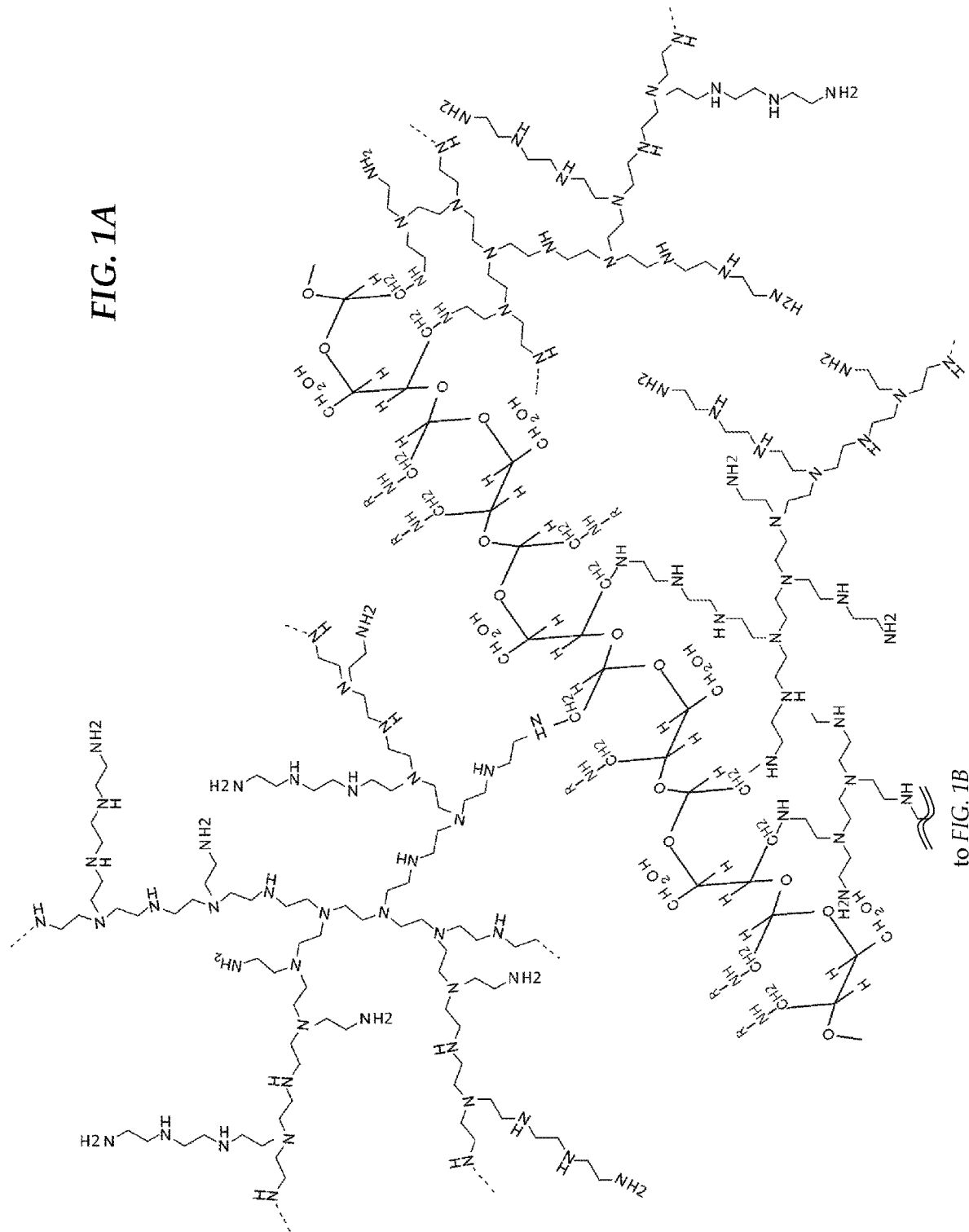
Figure 1B:
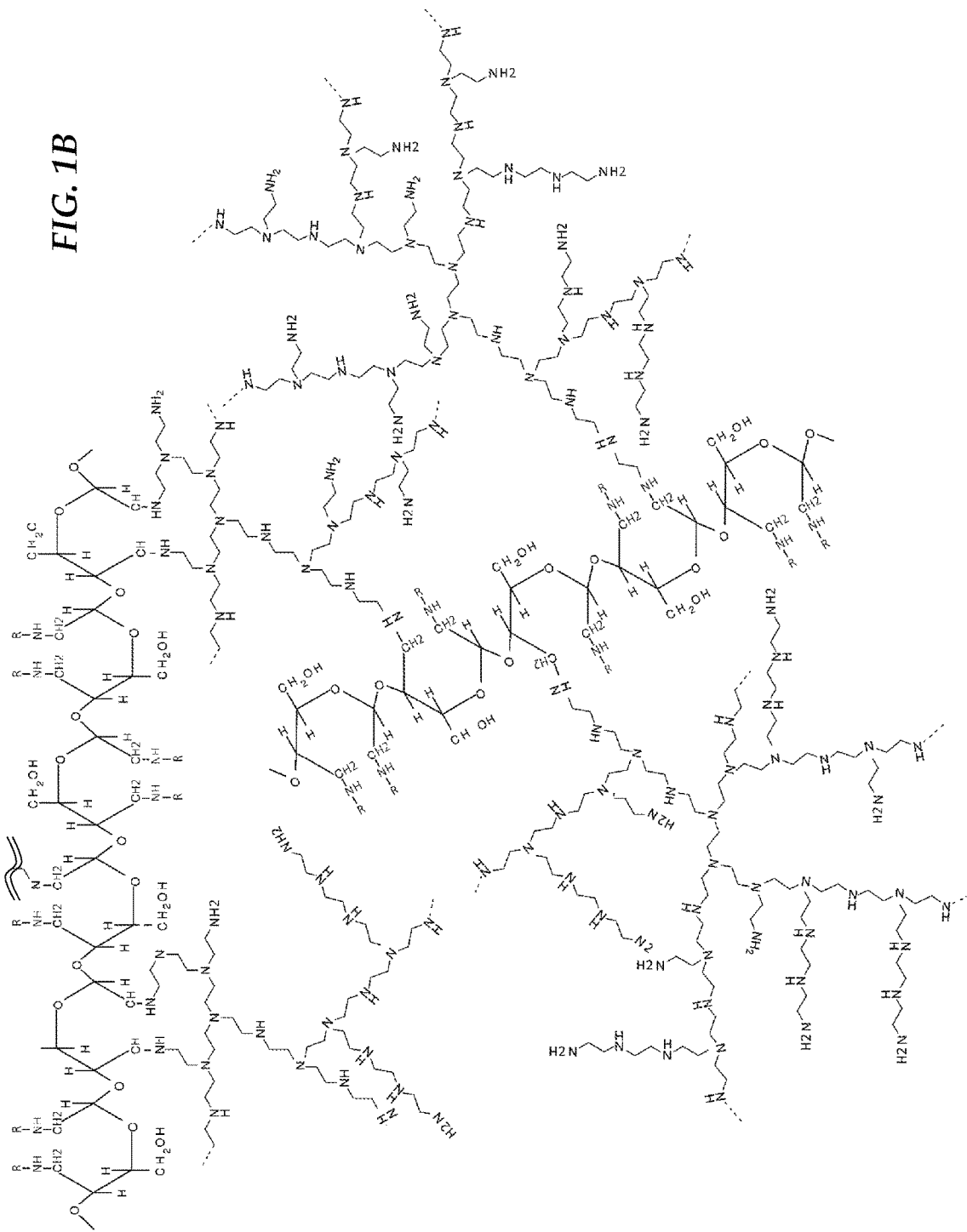

Generally, covalently cross-linked copolymers are described herein and may be used for a variety of purposes, including, but not limited to removal of phosphate. The covalently cross-linked copolymers generally include two components, namely, a backbone molecule and a functional polymer group cross-linked to the backbone molecule. In one approach, stable covalent bonds formed between a polysaccharide polymer and a large polymeric molecule provide a covalently cross-linked copolymer that have cationic functionality when the amino and/or imine functionality in the polymeric material is protonated.

In one form, the covalently cross-linked copolymer is a polysaccharide-polyamine copolymer. The polysaccharide-polyamine copolymers, when protonated, can form cationic copolymeric matrices having exceptionally high densities of cationic sites. In one form, the covalently cross-linked copolymers provide a three-dimensional structure, especially when hydrated. In some forms, the covalently cross-linked copolymer can be even more specifically characterized as polysaccharide-polyamine copolymers that include cellulose derived materials forming the polysaccharide component.

In one approach, a method of producing water insoluble polysaccharide-polyamine copolymers as described herein includes an oxidation reaction and a nucleophilic carbonyl addition reaction. In one approach, the oxidation reaction may involve oxidation of a saccharide, by one approach, a polysaccharide such as microcrystalline cellulose, amylopectin, starch, chitosan, chitin, dextran, glycogen, or the like.

In one aspect, the polysaccharide polymers are selected from the group consisting of selectively oxidized cellulose, selectively oxidized starch, selectively oxidized chitosan, selectively oxidized dextran, selectively oxidized glycogen, selectively oxidized chitin, and mixtures thereof. Selectively oxidized refers to having the hydroxyls at the C2 and C3 positions form di-aldehyde with concomitant cleavage of the C2-C3 bond where the oxidation will not produce more carboxyl groups than aldehyde groups and will not cleavage the polysaccharide chain.

In one form, preferred polysaccharides suitable for synthesis into copolymers are insoluble polysaccharides made of alpha-D-glucose units or D-glucosamine, bound to each other through β-1,4 glycosidic bonds, such as cellulose, amylose, chitosan, and chitin. Through the oxidization reaction, abundant aldehyde groups are generated on these polysaccharides by selectively oxidizing the hydroxyl groups on C2 and C3 of glucose units. These newly added hydrophilic aldehyde groups significantly increase the water solubility of oxidized polysaccharides. Further, the polysaccharide polymers are selected from the group consisting of oxidized cellulose, oxidized starch, oxidized chitosan, oxidized dextran, oxidized glycogen, oxidized chitin and mixtures thereof. Cellulose and chitosan contain β-1,4-glycosidic bond which cannot be digested by mammal. Starch, dextran and glycogen contain β-1,6-glycosidic bond and are digestible by human. However, the polysaccharide-polyamine polymeric matrices described herein are not digestible, regardless of the starting polysaccharide material.

The cross-linked copolymers may be prepared in a variety of manners. In one form, the preparation takes place in three steps. First, through an oxidation reaction, abundant aldehyde groups are generated on polysaccharides by selectively oxidizing the hydroxyl groups on C2 and C3 of the glucose units. In one form, selective oxidation generally means to oxidize the hydroxyl groups in the C2 and C3 positions to the corresponding aldehydes with the concomitant cleavage of the C2-C3 bond. Such oxidization will not produce more carboxyl groups than aldehyde groups and cause cleavage of the polysaccharide chain. A carboxyl group cannot covalently cross-link amine polymers under the conditions of the oxidation reaction, and that if formed carboxylic groups will undesirably form carboxylic acid in an aqueous environment. Further if formed, carboxylic acid will carry a negative charge which will undesirably interfere with the bonding of phosphate to the cationic charges formed when the amine groups are protonated.

The aldehyde groups generated by selective oxidation of the polysaccharides react with primary amines of amino polymers to form imine derivatives, the intermediate polysaccharide-polyamine copolymers with unstable carbon-nitrogen double bonds. In one form, these are considered di-block copolymers. Next, a reduction reaction is carried out to convert the carbon-nitrogen double bonds of the imines into the carbon-nitrogen single bonds of amines in order to produce the stable polysaccharide-polyamine copolymers.

According to one form, the polysaccharide-polyamine polymeric matrices are the result of the reaction of two pre-existing polymers or large molecules. In accordance with one form, the polysaccharide-polyamine copolymers may be considered di-block copolymers. In one form, the polysaccharide-polyamine copolymers are a reaction product of polysaccharide polymers having 2,3 di-aldehyde moieties and amino polymers having polyfunctional amino functionality reactive with the aldehyde moieties. The latter reaction product includes particulate covalently cross-linked polymers which are the polysaccharide-polyamine copolymers, such as cellulose-polyamine copolymers, having a three-dimensional structure. The amino functionality provides the cationic copolymers with cationic functionality when the amino functionality in the polysaccharide-polyamine copolymeric material is protonated.

It will be appreciated that the covalently cross-linked copolymers as described herein may also be produced by methods other than oxidation of polysaccharides and glycoproteins.

An intermediate polymer resulting from the above-discussed nucleophilic reaction may have the following general formula:

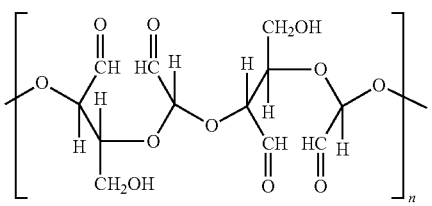

Figure 4:
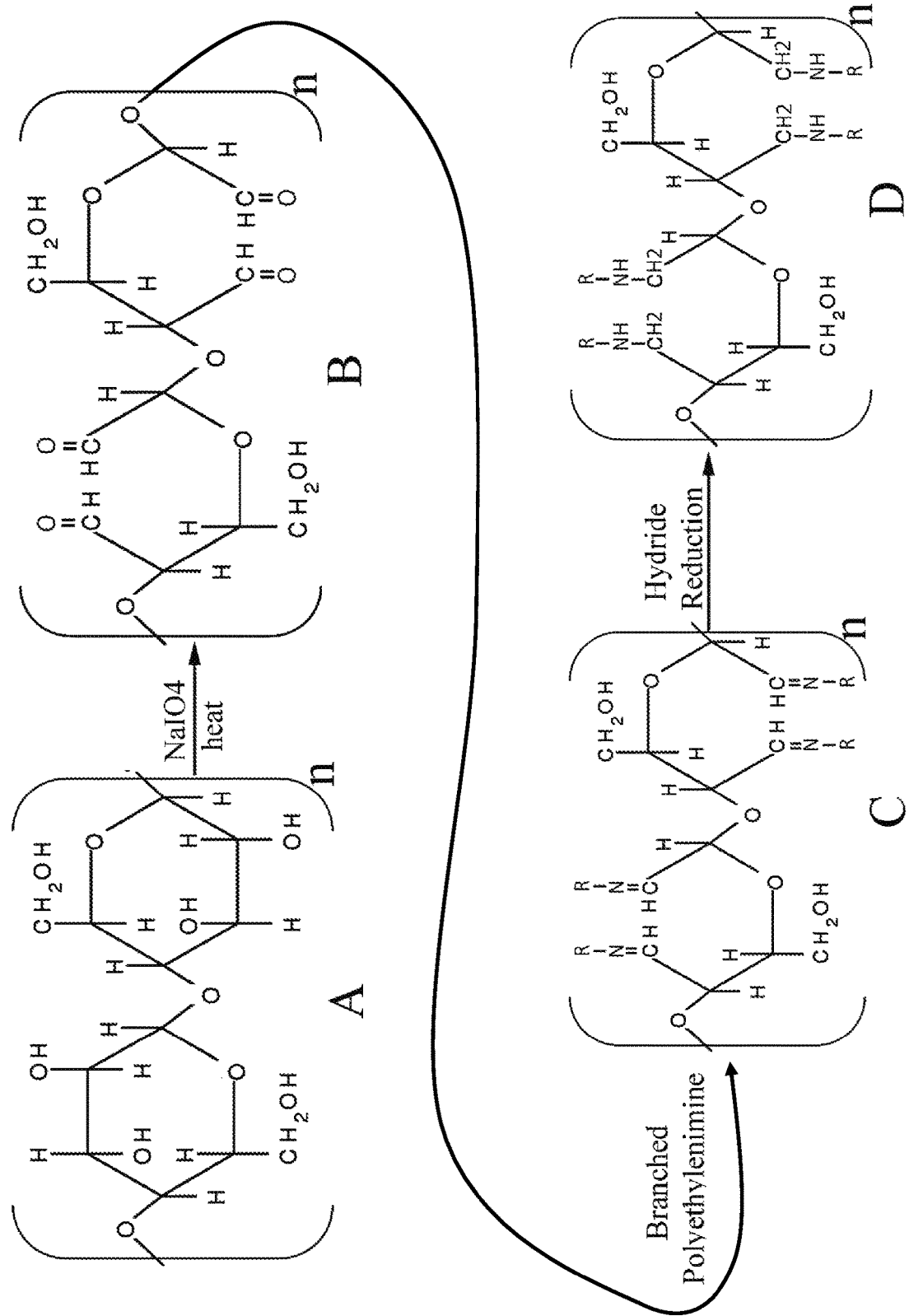
FIG. 4 is a schematic illustration of a method of obtaining an exemplary covalently cross-linked copolymer from cellulose.
Figure 5:
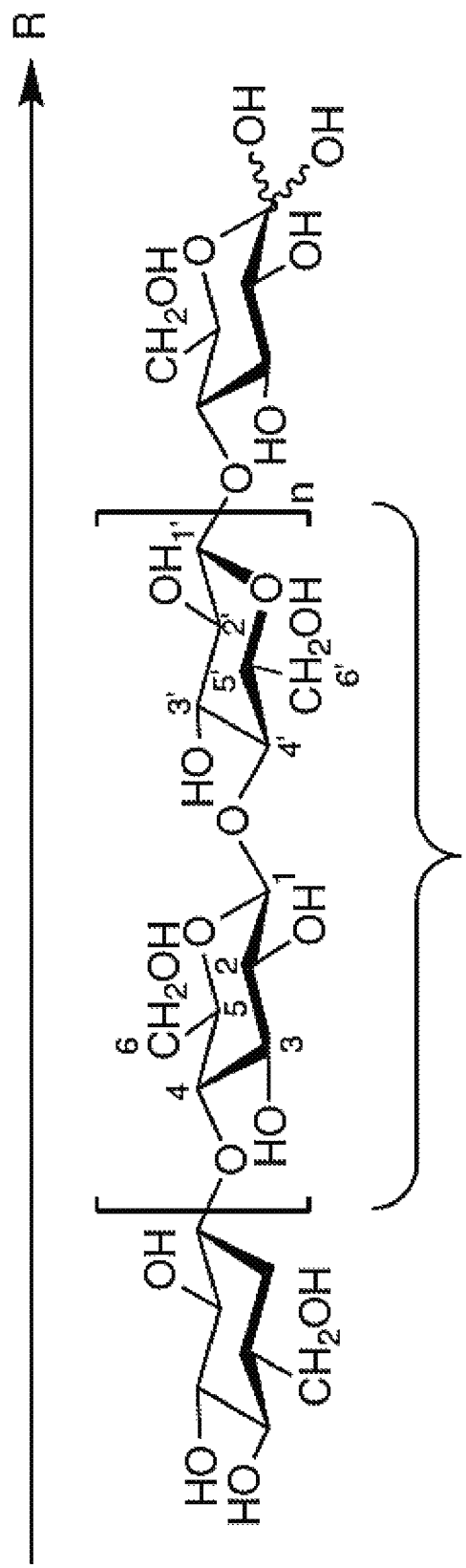
FIG. 5 is a general molecular structure of cellulose.
Figure 6A:
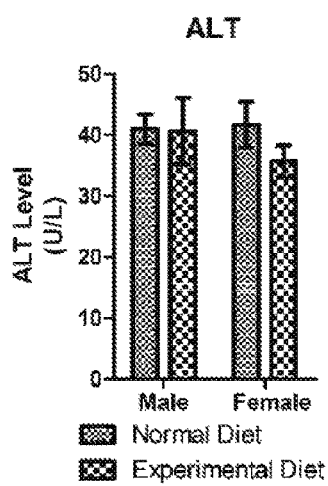
FIGS. 6A-6F are serum biochemistry assays.
Figure 6B:
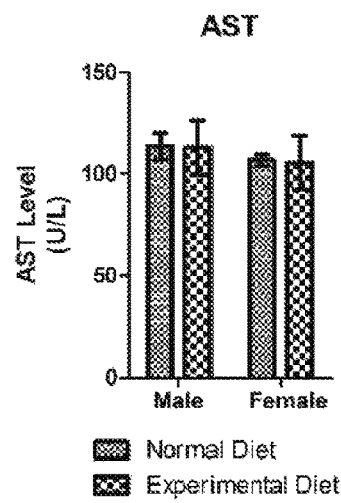
Figure 6C:
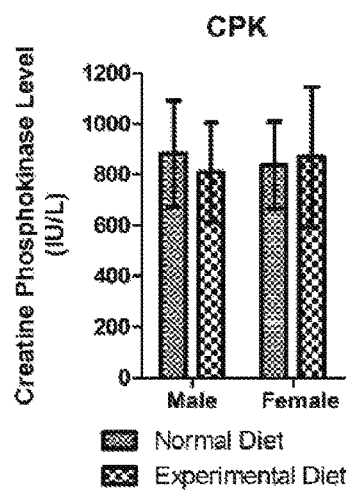
Figure 6D:
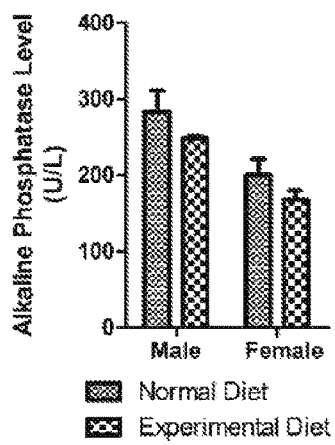
Figure 6E:
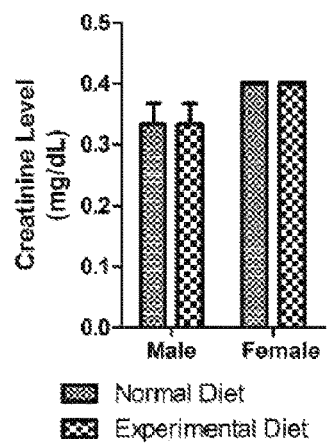
Figure 6F:
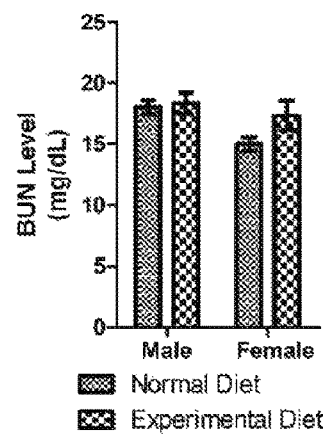
Figure 7:
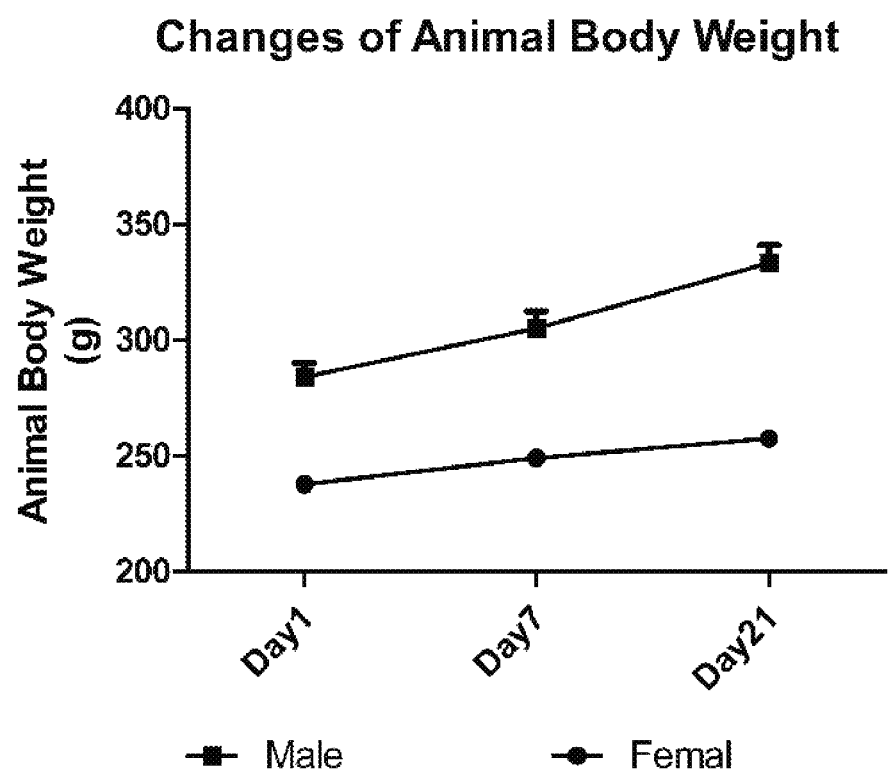
FIG. 7 is a graph of changes in animal body weight.

Reaction 1, shown in FIG. 4, shows a schematic illustration of a method of obtaining an exemplary polymer from cellulose. Cellulose is a naturally occurring polymer including glucose units interconnected by β-1,4-glycosidic bonds. The molecular structure of cellulose, which forms a backbone of the cellulose derivative polymer is generally represented in FIG. 5.

As seen in FIG. 4, a polysaccharide such as microcrystalline cellulose may be oxidized to form an intermediate of cellulose. In one approach, carbonyl group-enriched intermediates such as aldehydes are generated by the oxidization of the polysaccharide backbone. In particular, reactive aldehyde groups may be created by the opening of the cellulose ring at multiple sites along the polysaccharide backbone.

In FIG. 4, formula "A" generally represents cellulose, which may be any commercially available cellulose and formula "B" generally represents 2,3-dialdehyde that results from the oxidation of cellulose. As can be seen in FIG. 4, the 2,3-dialdehyde cellulose is a linear polymer with a structure similar to cellulose and includes one or more (and in the illustrated approach, two) reactive aldehyde groups. By one approach, cellulose may be pretreated with sulfuric acid to reduced crystallinity degree and size. In another approach, cellulose may be treated with hydrochloric acid.

While the exemplary chemical reaction in FIG. 4 utilizes sodium periodate (NaIO$_4$) as an oxidizing agent, it will be appreciated that the oxidation of cellulose may be alternatively catalyzed by periodic acid, potassium periodate, or other cationic derivatives and salts of periodic acid, or the like. Other non-selective oxidizing agents include chlorine, hydrogen peroxide, peracetic acid, chlorine dioxide, nitrogen dioxide, persulfates, permanganate, dichromate-sulfuric acid, hypochlorous acid, hypohalites or periodates, and a variety of metal catalysts. For the application described herein, non-selective oxidations are avoided. Oxidized polysaccharides including oxidized cellulose may contain carboxylic acid, aldehyde, and/or ketone groups, in addition to the original hydroxyl groups of the starting material, depending on the nature of the oxidant and reaction conditions.

Periodates, the stipulated and preferred oxidants, are a unique form of oxidants. Periodate-mediated oxidation of polysaccharides including cellulose is known to selectively oxidize the hydroxyl groups in the C2 and C3 positions to the corresponding aldehydes with the concomitant cleavage of the C2-C3 bond and is one of the most potent methods for polysaccharides modification. But other oxidants will produce more carboxyl groups than aldehyde groups and also cause cleavage of the chain of polysaccharides. The carboxyl group cannot covalently cross-link amine polymers under the reaction condition as described. Additionally, it will ionize and become carboxylic acid in aqueous solution. The carboxylic acid carries the negative charge and reduces the cationic polymer's reaction with other anions such as phosphate, a disturbance of the cationic function of the copolymers.

In one approach, the polymer intermediate formed as a result of the oxidation of polysaccharides as described above may then be subjected to nucleophilic carbonyl addition reactions with one or more branched cationic functional groups such as amino/imine polymers. Generally, polyfunctional primary amine-containing molecules can cross-link with the aldehyde-containing oligosaccharide derived from polysaccharides such as cellulose and the like or glycoproteins and the like. By one approach, a large molecular weight polyfunctional primary amine agent may be used to provide for the formation of a high density of cationic sites on the derivative saccharide when later protonated. For most approaches, any polyamine (both the linear and branched) containing multiple primary amines can be used as a nucleophilic reagent.

The above-described reaction of a high molecular weight polyamine such as polyethylenimine with an aldehyde group-containing saccharide derivative results in formation of stable covalent bonds between the amine polymer and a polysaccharide derived backbone molecule. In one form, this provides cross-linked copolymer generally represented by formula "C" above and discussed in more detail below. In the above-described exemplary reaction, the cellulose intermediate-containing reactive aldehyde groups formed as a result of the oxidation of cellulose with sodium periodate is subjected to a nucleophilic carbonyl addition reaction, such as with polyethylenimine to derive an exemplary insoluble cationic cellulose derivative polymer generally represented by formula "C.", obtained by a subsequent hydride reduction.

While the above-described exemplary reaction utilizes polyethylenimine as the nucleophilic agent, other exemplary polymers may be usable as nucleophiles in the reaction with the above-described intermediates of cellulose containing reactive aldehyde groups. Some exemplary cationic functional polymers include, for example, poly(allylamine), poly (amidoamine), polypropylenimine tetramine and the like. Polyethylenimine, poly(allylamine) and polypropylenimine tetramine are synthetic polyamine containing polymers that can be used in branched and/or dendrimer form.

In addition, branched or macrocyclic polyamines as described in International Publication No. WO 2014/029888, incorporated by reference herein in its entirety, may be suitable for the reactions as described herein. Furthermore, some exemplary linear polyamines suitable for the reactions described herein are listed below:

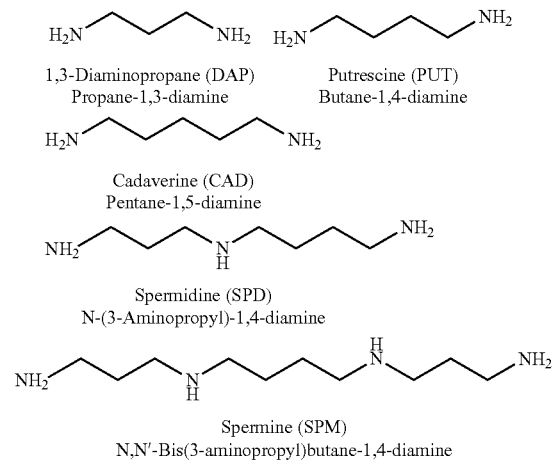

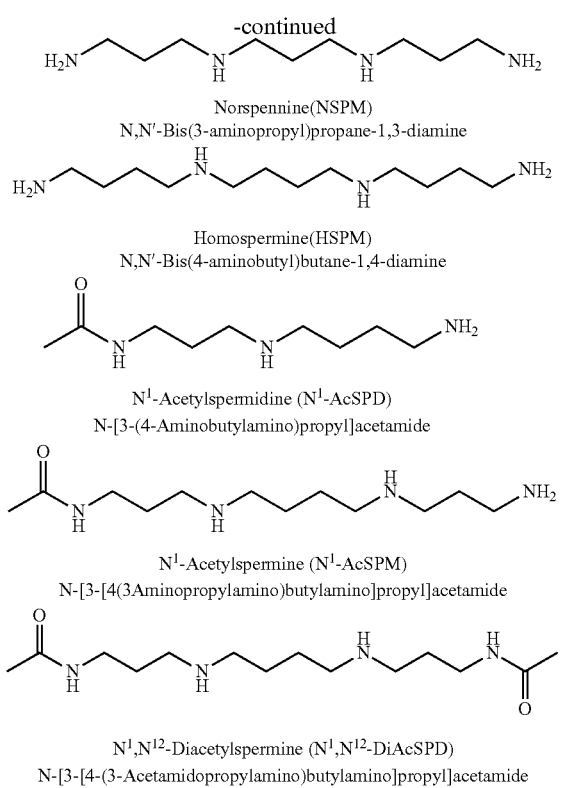

Norspennine(NSPM)
N,N'-Bis(3-aminopropyl)propane-1,3-diamine

Homospermine(HSPM)
N,N'-Bis(4-aminobutyl)butane-1,4-diamine $N^1$-Acetylspermidine ($N^1$-AcSPD)
N-[3-(4-Aminobutylamino)propyl]acetamide $N^1$-Acetylspermine ($N^1$-AcSPM)
N-[3-[4(3Aminopropylamino)butylamino]propyl]acetamide $N^1,N^{12}$-Diacetylspermine ($N^1,N^{12}$-DiAcSPD)
N-[3-[4-(3-Acetamidopropylamino)butylamino]propyl]acetamide After the above-described reaction of the polysaccharide derivative with a nucleophilic agent, the resulting product may be dried by evaporation or precipitation or other suitable technique. By one approach, polysaccharide-polyamine copolymer material of uniform particle size may be achieved by screening the dried material through a suitable mesh. When in particulate form, the pores in the polysaccharide-polyamine copolymeric matrix and/or protonated polysaccharide-polyamine copolymeric matrix range in size of less than 50 μm, and in an important aspect from about hundreds of nanometer to about 50 μm.

By one approach, the amino density of the resulting cationic copolymers is also controlled by the degree of polymerization, size of the nucleophile and the relative ratio of the polysaccharide substrate backbone and nucleophile. As used in this application, charge density refers to the number of protonated sites, such as from primary, secondary, and/or tertiary amines, within the cationic polymer. More specifically, the charge carrier density refers to the number of charge carriers (e.g., electrons, ions) in a material (e.g., cationic polymers) per unit volume, not the actual charges on the carriers. According to one form, the polysaccharide-polyamine is prepared to provide the cross-linked structure having a nitrogen content of at least 12.5 wt. %, based upon the weight of the polysaccharide copolymer. In an important aspect the dendrimer has a nitrogen content of at least 30 wt. % based upon the weight of the dendrimer which is effective to provide the polysaccharide-polyamine polymeric material when protonated (which results in the cationic polymer matrix) with a nitrogen content of at least about 12 wt. %, and preferably in the range of 20-30 wt. %, based upon the weight of the cationic material.

The ranges may be qualitatively described as low, moderate, and high based on the molar ratios of the aldehyde-containing saccharide derivative and the functional primary amine nucleophile. In one approach, the aldehyde content and the primary amine content of the reactants are determined by quantitative titrimetry, while the NH2+ content of the final product is determined by Nuclear Magnetic Resonance Spectroscopy (NMR).

Figure 2:
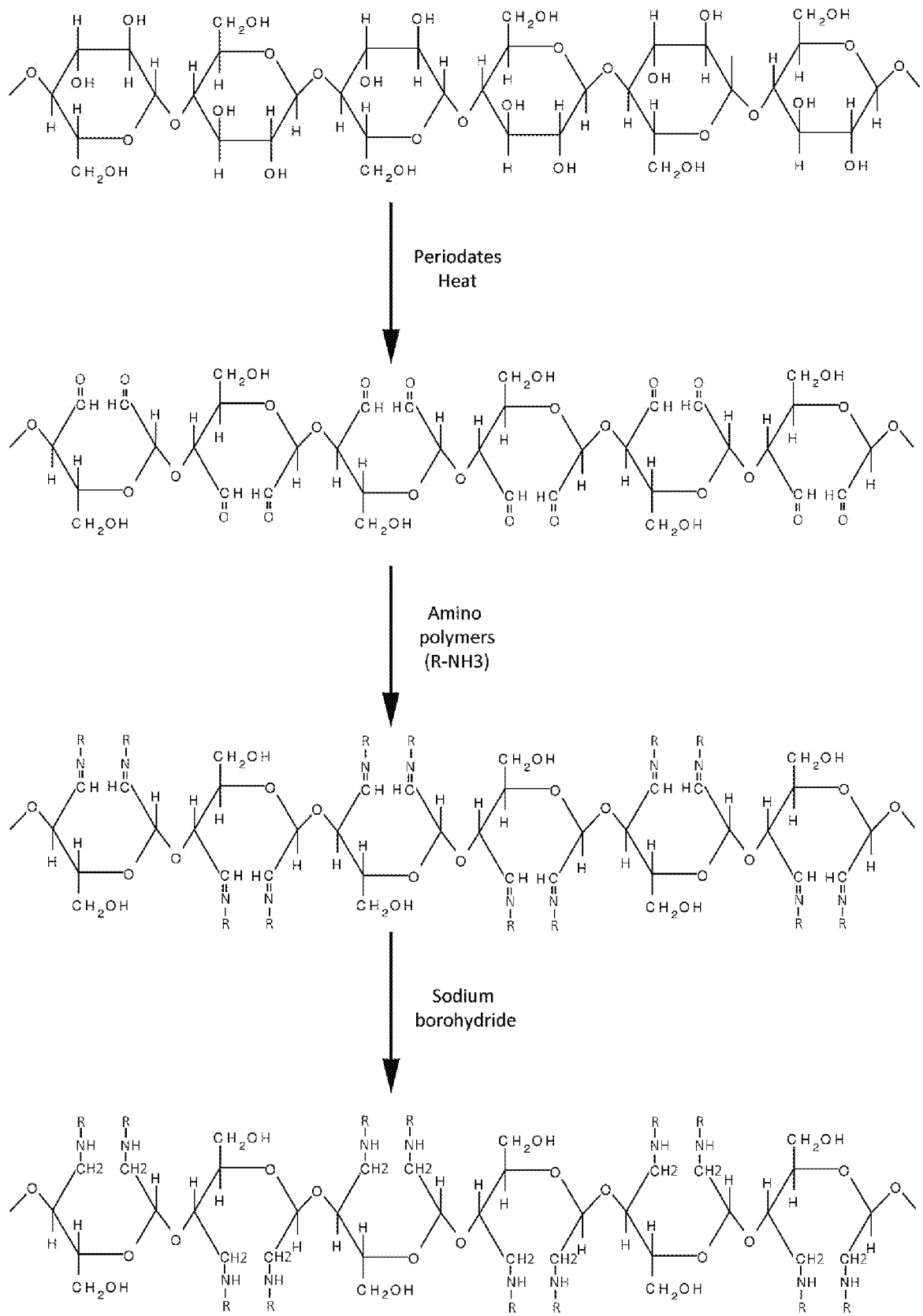
FIG. 2 is a schematic illustration of synthesis of exemplary covalently cross-linked copolymers using a polysaccharide backbone.
Figure 3A:
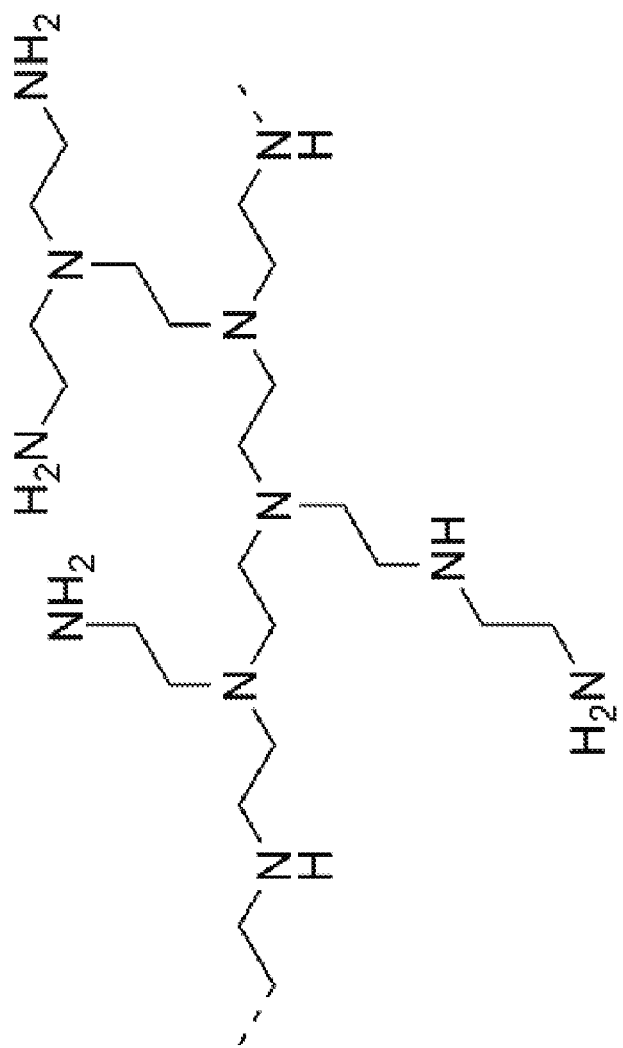
FIG. 3A is an example of branched polyethylenimine.
Figure 3B:
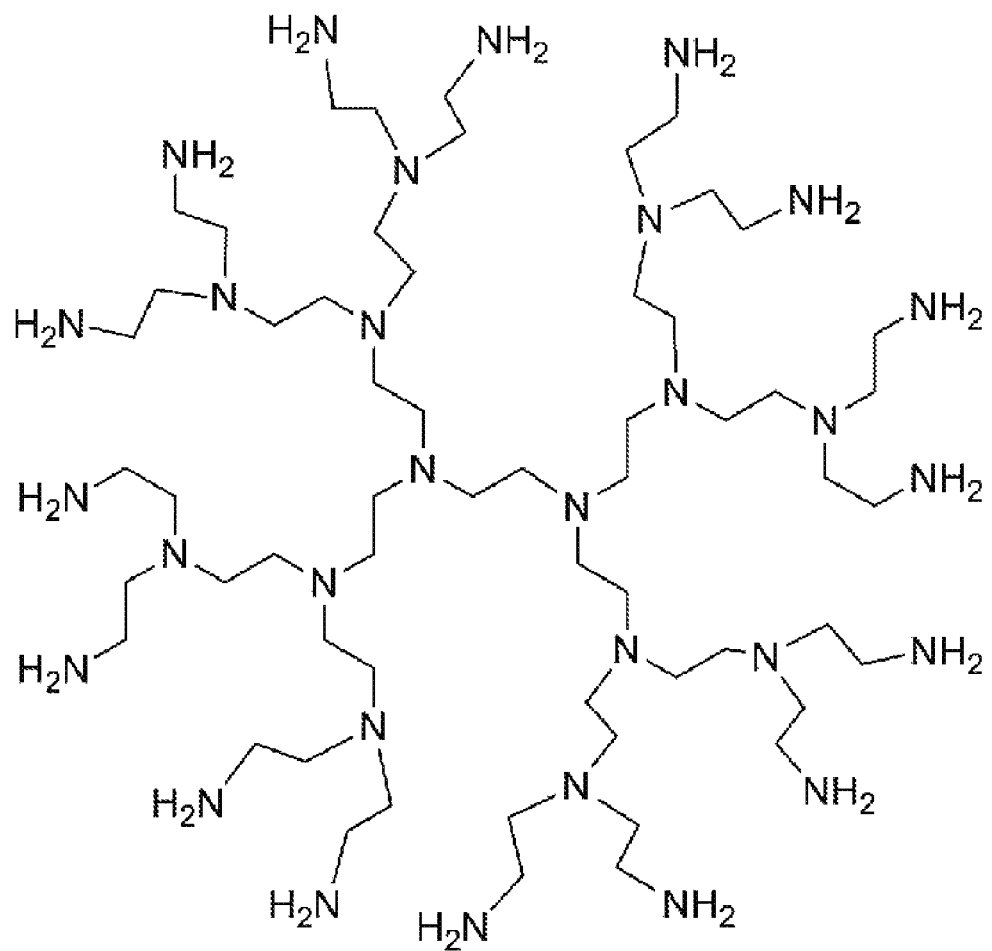
FIG. 3B is an example of dendritic polyethylenimine.

Another exemplary process is provided in FIG. 2 illustrating the reaction of polysaccharides with amino materials.

The physical characteristics of the covalently cross-linked copolymer resulting from the above-described oxidation and nucleophilic carbonyl addition reaction may be controlled by manipulating the conditions of the above-described reaction, for example, by varying the relative ratios of the substrate backbone and nucleophile, varying the types of functional groups used for reaction with the substrate backbone, and/or varying the time, pH, and/or temperature of the reaction. For example, increasing the temperature at which the reaction is run can lead to a corresponding increase in the size of the resulting water insoluble cationic copolymer. In another example, increasing the reaction time can lead to a corresponding increase in the size of the resulting water insoluble cationic copolymer. In yet another example, increasing the pH of the reaction conditions can lead to a corresponding increase in the size of the resulting covalently cross-linked copolymer. In still yet another example, the size of the resulting covalently cross-linked copolymer product can be controlled via selection of the molecular weight and ratios of the two major reactants, namely, the derivative polysaccharide (e.g., 2,3-dialdehyde cellulose) and the polyamine nucleophile (e.g., polyethylenimine).

In one approach, poly(allylamine) (PLA) with an average molecular weight of about 15,000 Da to about 900,000 Da or polyethylimine (PEI) with an average molecular weight of about 25,000 Da to about 750,000 Da can be used. For example, PLA with an average molecular weight of approximately 15,000 Da, 17,000 Da, 65,000 Da, or 900,000 Da, or PEI with an average molecular weight of approximately 25,000 Da or 750,000 Da obtained from Sigma-Aldrich may be used. The ratio of the polysaccharide backbone component (e.g., cellulose) to the cationic site forming functional polymer (e.g., polyethylenimine) used in the reaction may depend upon the molecular weight of the cationic site forming functional polymer. For example, for PEI and PLA with molecular weight from about 15,000 Da to about 25,000 Da, the ratio of the derivative cellulose to polyamine may range from about 1:1 to about 1:8. In one approach, when PEI and PLA with molecular weight ranging from about 65,000 to about 750,000 is used, the ratio of the derivative cellulose to polyamine ranges from about 1:5 to about 1:20.

In one aspect the amino polymers are dendrimers which are macromolecular amines that have a core or center which includes amine groups and branches that include these functional groups which may be formed through a series of iterative reactions starting with the functional groups at the core or center to provide a highly branched amine polymer. In one aspect, the dendrimer molecule may be round or substantially round or have a three-dimensional morphology which is spherical or has an outer perimeter which is curvilinear or bounded by curved lines. In an important aspect the dendrimer has a nitrogen content of at least 30 wt. % based upon the weight of the dendrimer which is effective to provide the polysaccharide-polyamine copolymeric material when protonated (which results in the cationic polymer matrix) with a nitrogen content of at least about 10 wt. %, and preferably in the range of 20-30 wt. %, based upon the weight of the cationic material. In another form, branched forms of the amino polymers may also be used alone or in combination with the dendrimeric forms.

The particle size of the cross-linked copolymer product may be regulated by coupling the cross-linking polyfunctional primary amines (e.g., polyethylenimine) with polysaccharide derivatives (2,3-dialdehyde cellulose) having low, intermediate, and very high molecular weights (e.g., ranging from about 15,000 Da to 750,000 Da) to obtain nanoparticles, microparticles, and millimeter sized particles.

The polysaccharide-polyamine copolymeric matrices are three-dimensional cross-linked matrices of polysaccharide polymers linked together with the polyamino polymers, especially when hydrated. These three-dimensional structure of covalently cross-linked copolymers are in a particulate form, the particulates having a size in the range of from about 100 μm to about 10 mm. The dehydrated form of the polysaccharide-polyamine copolymers or copolymeric matrices does not carry any permanent charges. These copolymers contain abundant amine groups and a small amount of imino groups. Amines and imine are classified as weak bases with pKa value in the range of from 9 to 11. When exposed to an aqueous environment with a pH lower than 9.0, the polysaccharide-polyamine copolymers or copolymeric matrices will be rehydrated, swelled, protonated and formed a cationic copolymeric matrix.

The polysaccharide polymers, such as cellulose, starch, chitosan, dextran, glycogen, and chitin, are oxidized in an amount effective to provide the 2,3 aldehyde moiety which is reactive with the amino polymers to permit the oxidized polymers to react with polyamino functional polymers which in turn provide the covalently cross-linked structure having a nitrogen content of at least 12.5 weight percent, based upon the weight of the polysaccharide copolymer. The amino polymers cross-link the polysaccharide polymers, such as water soluble cellulosic polymers (having the di-aldehyde moieties) to provide the three-dimensional structure of polysaccharide-derived "backbones" where multiple polysaccharide chains are linked with multiple chains of the amino polymers. These polysaccharide polymers are pre-existing polymers which are "blocks" or "backbones" linked together by pre-existing amino polymers which also are discrete amino blocks. In one form, the polysaccharide-polyamine copolymers may be considered to be di-block copolymers. The linked backbones are bonded together as the covalently cross-linking products of the amine polymers (which form cross-linking blocks) and the selectively oxidized polysaccharide to provide cross-linked block copolymer and copolymeric matrices with high percent of amine content which may be protonated.

The resulting cross-linked copolymer, such as a polysaccharide-polyamine copolymer, may be prepared in the form of a solid powder, a gel, and the like. Further, the cross-linked copolymer may have a phosphate binding capacity of 2.59±0.43 mmol/g, when the phosphate level is 6.25 mM at pH 7 in vitro. In one form, at pH 6, the cross-linked copolymer has the maximum phosphate binding capacity of 2.56±0.27 mmol/g, when the phosphate concentration is 5 mM, the physiological phosphate level, in vitro. According to one form, the cross-linked copolymer may show a stable phosphate binding property after storage in water at room temperature for at least 3 months. According to one form, the swell factor of the covalently cross-linked copolymer may be about 6.43±0.36 fold.

It should be appreciated that natural raw materials containing cellulose, such as wheat stems, straw, wood chips, etc. can be transformed into derivatives useful in the preparation of covalently cross-linked copolymers, such as cellulose-polyamine copolymers.

The covalently cross-linked copolymer can be used for a variety of purposes. Methods of removal of phosphate compounds from the human body and other mammalian bodies also are described herein. The methods include the oral administration of the polysaccharide-polyamine copolymeric material and/or cationic copolymeric material having exceptionally high densities of cationic sites. The in vitro phosphate binding capacity assay show the polysaccharide-polyamine copolymer has similar phosphate binding capacity as Sevelamer. The administration of these compounds permit removal of at least more phosphate than administering the same amount under the same conditions (including pH) of cellulose cross linked with epichlorohydrin.

A biocompatible cationic polymer is produced to sustain a high positive charge density resulting in strong bonding of polyvalent anions including phosphate negatively charged peptides, and anions of metals, etc. The high purity GMP grade material can be formulated into a drug for treatment of hyperphosphatemia, induced by chronic kidney diseases.

Furthermore, the covalently cross-linked copolymer can be used as a high capacity anion-exchanger to remove nitrates, phosphates, and metal anions from waste/run-off water for the purpose of the preventing environmental pollution. In another form, the covalently cross-linked copolymer can be used as a drug or membrane for phosphate binding such as for hyperphsophatemia.

EXAMPLES

Example 1

Soluble 2,3-dialdehyde cellulose (DAC) was prepared by sodium periodate oxidation of cellulose (oxidized glucose unite >80%). 10 g cellulose (size: <100 nm, 20 μm, 50 m or fiber) was resuspended with 200 mL deionized water. Next, 20 g sodium periodate was added and then the pH was adjusted to a pH of 3.0 with 6×HCl. Next, the composition was degassed and purged with nitrogen gas and then allowed to react at 60° C. with stirring for 4 hours in dark at pH 3. The reaction was stopped by adding 10 mL of ethylene glycol. Dialysis the product against deionized water for 3 days. The soluble DAC was collected as supernatant by centrifugation at 40,000 g for 30 minutes to remove insoluble DAC as pallets. The collected supernatant was freeze dried (optional).

Example 2

Insoluble 2,3-dialdehyde cellulose (DAC) was prepared by sodium periodate oxidation of cellulose (oxidized glucose unite <80%). 10 g cellulose (size: <100 nm, 20 m, 50 m or fiber) was resuspended with 200 mL deionized water. Next, 10 g of sodium periodate was added and then the pH was adjusted to a pH of 3.0 with 6×HCl. Next, the composition was degassed and purged with nitrogen gas and then allowed to react at 60° C. with stirring for 4 hours in dark at pH 3. The reaction was stopped by adding 10 mL of ethylene glycol. The product was washed with deionized water. Insoluble DAC was collected by centrifugation at 2,000 g for 10 minutes. The washed insoluble DAC solution was then resuspended with DI water. The washed insoluble DAC solution was freeze dried (optional).

In one form, different ratios of DAC to poly(allylamine) hydrochloride (PLA) and/or polyethyleneimine (PEI) may be used. Some exemplary ratios for different forms of PEI and PLA are shown below in Table 1.

TABLE 1

| Type of branched PEI or PLA | The ratios (W/W) of DAC to PEI or PLA allowing to produce material in hydrogel form |
|---|---|
| PEI MW 25K | 1:1 to 1:3 |
| PEI MW 750K | 1:10 to 1:30 |
| PLA MW 15K | 1:1 to 1:5 |
| PLA MW 58K | 1:5 to 1:20 |

Example 3

Polysaccharide-polyamine copolymers in hydrogel form (CellPhos) were synthesized by reacting DAC with branched PEI (MW 750K). The ratio of DAC to PEI was 1:10 and the reaction was performed without alcohol. The branched polyethyleneimine, 45 g, (MW 750K, 50 wt. % in H$_2$O) was added into a 500 mL beaker. The pH of PEI was adjusted to 1.0 with 37% HCl. Five grams of branched polyethyleneimine (MW 750K, 50 wt. % in H$_2$O) were added into a 50 ml centrifuge tube and diluted with equal volume deionized water. The pH of 100 ml of DAC solution, containing 5 g of soluble DAC, was adjusted to 1.0 by adding 6×HCl. The solutions of PEI and solution of DAC were incubated on ice for 10 minutes. The solution containing 45 g of PEI and solution containing 5 g of DAC were mixed and incubated on ice for 10 minutes with stirring. The solution containing 5 g diluted PEI was quickly added into the PEI-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass a mesh screen to achieve gel particles with a uniform size. Deionized water was added to bring the total volume of gel particles suspension to 1000 ml. The gel particles suspension was incubated at 70° C. for an additional 60 minutes. The pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 solution for 60 minutes with stirring and precipitated by gravity at room temperature. After the supernatant was aspirated, the precipitated gel particles were washed with 4 liters of deionized water for two times and precipitated by gravity. After the supernatant was aspirated, the precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 4

Polysaccharide-polyamine copolymers in hydrogel form were synthesized by reacting DAC with branched PEI (MW 750K). The ratio of DAC to PEI was 1:20. The condition of reaction was without alcohol. The branched polyethyleneimine, 45 g, (MW 750K, 50 wt. % in H$_2$O) was added into a 500 mL beaker. The pH of PEI was adjusted to 1.0 with 37% HCl. Five grams of branched polyethyleneimine (MW 750K, 50 wt. % in H$_2$O) were added into a 50 ml centrifuge tube and diluted with equal volume deionized water. The pH of 100 ml of DAC solution, containing 2.5 g of soluble DAC, was adjusted to 1.0 by adding 6×HCl. The solutions of PEI and solution of DAC were incubated on ice for 30 minutes. The solution containing 45 g of PEI and solution containing 2.5 g of DAC were mixed and incubated on ice for 10 minutes with stirring. The solution containing 5 g diluted PEI was quickly added into a PEI-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass a mesh screen to achieve gel particles with a uniform size. Deionized water was added to bring the total volume of gel particles suspension to 1000 ml. The gel particles suspension was incubated at 70° C. for an additional 60 minutes. The pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 solution for 60 minutes with stirring and precipitated by gravity at room temperature. After the supernatant was aspirated, the precipitated gel particles were washed with 4 liters deionized water for two times and precipitated by gravity. After the supernatant was aspirated, the precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 5

Polysaccharide-polyamine copolymers in hydrogel form were synthesized by reacting DAC with branched PEI (MW 750K). The ratio of DAC to PEI was 1:30. The condition of reaction was without alcohol. The branched polyethyleneimine, 45 g, (MW 750K, 50 wt. % in H$_2$O) was added into a 500 mL beaker. The pH of PEI was adjusted to 1.0 with 37% HCl. Five grams of branched polyethyleneimine (MW 750K, 50 wt. % in H$_2$O) were added into a 50 ml centrifuge tube and diluted with equal volume deionized water. The pH of 100 ml of DAC solution, containing 1.67 g of soluble DAC, was adjusted to 1.0 by adding 6×HCl. The solutions of PEI and solution of DAC were incubated on ice for 30 minutes. The solution containing 45 g of PEI and solution containing 1.67 g of DAC were mixed and incubated on ice for 10 minutes with stirring. The solution containing 5 g diluted PEI was quickly added into a PEI-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass through a mesh screen to achieve gel particles with a uniform size. Deionized water was added to bring the total volume of gel particles suspension to 1000 ml. The gel particles suspension was incubated at 70° C. for an additional 60 minutes. The pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 solution for 60 minutes with stirring and precipitated by gravity at room temperature. After the supernatant was aspirated, the precipitated gel particles were washed with 4 liters deionized water twice and precipitated by gravity.

After the supernatant was aspirated, the precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 6

Polysaccharide-polyamine copolymers in hydrogel form were synthesized by reacting DAC with branched PEI (MW 25K). The ratio of DAC to PEI was 1:1. The condition of reaction was without alcohol. The branched polyethyleneimine, 45 g, (MW 25K) was added into a 500 mL beaker. The pH of PEI was adjusted to 1.0 with 37% HCl. Five grams of branched polyethyleneimine (MW 25K) were added into a 50 ml centrifuge tube and diluted with equal volume deionized water. The pH of 100 ml of DAC solution, containing 50 g of soluble DAC, was adjusted to 1.0 by adding 6×HCl. The solutions of PEI and solution of DAC were incubated on ice for 30 minutes. The solution containing 45 g of PEI and solution containing 50 g of DAC were mixed and incubated on ice for 10 minutes with stirring. The solution containing 5 g diluted PEI was quickly added into a PEI-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass through a mesh screen to achieve gel particles with a uniform size. Deionized water was added to bring the total volume of gel particles suspension to 1000 ml. The gel particles suspension was incubated at 70° C. for an additional 60 minutes. The pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 solution for 60 minutes with stirring and precipitated by gravity at room temperature. After the supernatant was aspirated, the precipitated gel particles were washed with 4 liters deionized water twice and precipitated by gravity. After the supernatant was aspirated, the precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 7

Polysaccharide-polyamine copolymers in hydrogel form were synthesized by reacting DAC with branched PEI (MW 25K). The ratio of DAC to PEI was 1:3. The condition of reaction was without alcohol. The branched polyethyleneimine, 45 g, (MW 25K) was added into a 500 mL beaker. The pH of PEI was adjusted to 1.0 with 37% HCl. Five grams of branched polyethyleneimine (MW 25K) were added into a 50 ml centrifuge tube and diluted with equal volume deionized water. The pH of 100 ml of DAC solution, containing 16.7 g of soluble DAC, was adjusted to 1.0 by adding 6×HCl. The solutions of PEI and solution of DAC were incubated on ice for 30 minutes. The solution containing 45 g of PEI and solution containing 16.7 g of DAC were mixed and incubated on ice for 10 minutes with stirring. The solution containing 5 g diluted PEI was quickly added into a PEI-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass through a mesh screen to achieve gel particles with a uniform size. Deionized water was added to bring the total volume of gel particles suspension to 1000 ml. The gel particles suspension was incubated at 70° C. for an additional 60 minutes. The pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 solution for 60 minutes with stirring and precipitated by gravity at room temperature. After the supernatant was aspirated, the precipitated gel particles were washed with 4 liters deionized water twice and precipitated by gravity. After the supernatant was aspirated, the precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 8

Polysaccharide-polyamine copolymers in hydrogel form were synthesized by reacting DAC with branched PEI (MW 750K). The ratio of DAC to PEI was 1:10. The condition of reaction was with alcohol. The branched polyethyleneimine, 45 g, (MW 750K, 50 wt. % in $H_2O$) was added into a 500 mL beaker. The pH of PEI was adjusted to 1.0 with 37% HCl. Five grams of branched polyethyleneimine (MW 750K, 50 wt. % in $H_2O$) were added into a 50 ml centrifuge tube and diluted with equal volume deionized water. The pH of 100 ml of DAC solution, containing 5 g of soluble DAC, was adjusted to 1.0 by adding 6×HCl. The solutions of PEI and solution of DAC were incubated on ice for 30 minutes. The solution containing 45 g of PEI and solution containing 5 g of DAC were mixed and incubated on ice for 10 minutes with stirring. The solution containing 5 g diluted PEI was quickly added into a PEI-DAC mixture and incubated on ice with stirring at 1000 RPM for 5 minutes. The mixture was kept on ice without agitation until the hydrogel was completely formed. The hydrogel was incubated at 70° C. for an additional 60 minutes. The hydrogel was forced to pass through a mesh screen to achieve gel particles with a uniform size. Absolute alcohol was added to bring the total volume of gel particles suspension to 1000 ml. The gel particles suspension was incubated at 70° C. for an additional 60 minutes. The pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 solution for 60 minutes with stirring and precipitated by gravity at room temperature. After the supernatant was aspirated, the precipitated gel particles were washed with 4 liters deionized water twice and precipitated by gravity. After the supernatant was aspirated, the precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 9

Polysaccharide-polyamine copolymers in hydrogel form were synthesized by reacting DAC with branched PEI (MW 750K). The ratio of DAC to PEI was 1:20. The condition of reaction was with alcohol. The branched polyethyleneimine, 45 g, (MW 750K, 50 wt. % in $H_2O$) was added into a 500 mL beaker. The pH of PEI was adjusted to 1.0 with 37% HCl. Five grams of branched polyethyleneimine (MW 750K, 50 wt. % in $H_2O$) were added into a 50 ml centrifuge tube and diluted with equal volume deionized water. The pH of 100 ml of DAC solution, containing 2.5 g of soluble DAC, was adjusted to 1.0 by adding 6×HCl. The solutions of PEI and solution of DAC were incubated on ice for 30 minutes. The solution containing 45 g of PEI and solution containing 2.5 g of DAC were mixed and incubated on ice for 10 minutes with stirring. The solution containing 5 g diluted PEI was quickly added into a PEI-DAC mixture and incubated on ice with stirring at 1000 RPM for 5 minutes. The mixture was kept on ice without agitation until the hydrogel was completely formed. The hydrogel was incubated at 70° C. for an additional 60 minutes. The hydrogel was forced to pass through a mesh screen to achieve gel particles with a uniform size with different diameters. Absolute alcohol was added to bring the total volume of gel particles suspension to 1000 ml. The gel particles suspension was incubated at 70° C. for an additional 60 minutes. The pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 solution for 60 minutes with stirring and precipitated by gravity at room temperature. After the supernatant was aspirated, the precipitated gel particles were washed with 4 liters deionized water twice and precipitated by gravity. After the supernatant was aspirated, the precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 10

Polysaccharide-polyamine copolymers in hydrogel form were synthesized by reacting DAC with branched PEI (MW 750K). The ratio of DAC to PEI was 1:30. The condition of reaction was with alcohol. The branched polyethyleneimine, 45 g, (MW 750K, 50 wt. % in $H_2O$) was added into a 500 mL beaker. The pH of PEI was adjusted to 1.0 with 37% HCl. Five grams of branched polyethyleneimine (MW 750K, 50 wt. % in $H_2O$) were added into a 50 ml centrifuge tube and diluted with equal volume deionized water. The pH of 100 ml of DAC solution, containing 1.67 g of soluble DAC, was adjusted to 1.0 by adding 6×HCl. The solutions of PEI and solution of DAC were incubated on ice for 30 minutes. The solution containing 45 g of PEI and solution containing 5 g of DAC were mixed and incubated on ice for 10 minutes with stirring. The solution containing 5 g diluted PEI was quickly added into a PEI-DAC mixture and incubated on ice with stirring at 1000 RPM for 5 minutes. The mixture was kept on ice without agitation until the hydrogel was completely formed. The hydrogel was incubated at 70° C. for an additional 60 minutes. The hydrogel was forced to pass through a mesh screen to achieve gel particles with a uniform size with different diameters. Absolute alcohol was added to bring the total volume of gel particles suspension to 1000 ml. The gel particles suspension was incubated at 70° C. for an additional 60 minutes. The pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 solution for 60 minutes with stirring and precipitated by gravity at room temperature. After the supernatant was aspirated, the precipitated gel particles were washed with 4 liters deionized water twice and precipitated by gravity. After the supernatant was aspirated, the precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 11

Cationic polymers in hydrogel form were synthesized by reacting DAC with branched PEI (MW 25K). The ratio of DAC to PEI was 1:1. The condition of reaction was with alcohol. The branched polyethyleneimine, 45 g, (MW 25K) was added into a 500 mL beaker. The pH of PEI was adjusted to 1.0 with 37% HCl. Five grams of branched polyethyleneimine (MW 25K) were added into a 50 ml centrifuge tube and diluted with equal volume deionized water. The pH of 100 ml of DAC solution, containing 50 g of soluble DAC, was adjusted to 1.0 by adding 6×HCl. The solutions of PEI and solution of DAC were incubated on ice for 30 minutes. The solution containing 45 g of PEI and solution containing 50 g of DAC were mixed and incubated on ice for 10 minutes with stirring. The solution containing 5 g diluted PEI was quickly added into a PEI-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass through a mesh screen to achieve gel particles with a uniform size with different diameters. Absolute alcohol was added to bring the total volume of gel particles suspension to 1000 ml. The gel particles suspension was incubated at 70° C. for an additional 60 minutes. The pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 solution for 60 minutes with stirring and precipitated by gravity at room temperature. After the supernatant was aspirated, the precipitated gel particles were washed with 4 liters deionized water twice and precipitated by gravity. After the supernatant was aspirated, the precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 12

Cationic polymers in hydrogel form were synthesized by reacting DAC with branched PEI (MW 25K). The ratio of DAC to PEI was 1:3. The condition of reaction was with alcohol. The branched polyethyleneimine, 45 g, (MW 25K) was added into a 500 mL beaker. The pH of PEI was adjusted to 1.0 with 37% HCl. Five grams of branched polyethyleneimine (MW 25K) were added into a 50 ml centrifuge tube and diluted with equal volume deionized water. The pH of 100 ml of DAC solution, containing 16.7 g of soluble DAC, was adjusted to 1.0 by adding 6×HCl. The solutions of PEI and solution of DAC were incubated on ice for 30 minutes. The solution containing 45 g of PEI and solution containing 16.7 g of DAC were mixed and incubated on ice for 10 minutes with stirring. The solution containing 5 g diluted PEI was quickly added into a PEI-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass through a mesh screen to achieve gel particles with a uniform size with different diameters. Absolute alcohol was added to bring the total volume of gel particles suspension to 1000 ml. The gel particles suspension was incubated at 70° C. for an additional 60 minutes. The pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 solution for 60 minutes with stirring and precipitated by gravity at room temperature. After the supernatant was aspirated, the precipitated gel particles were washed with 4 liters deionized water twice and precipitated by gravity. After the supernatant was aspirated, the precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 13

Polysaccharide-polyamine copolymers in particle form were directly synthesized through titration of the insoluble DAC without alcohol. The 50 g branched polyamines including poly(allylamine hydrochloride) (MW 58K and 15K) or polyethyleneimine (MW 750K and 25K) were dissolved in deionized water to get 100 ml of total volume. The pH of the solution was adjusted to 9.0 with 37% HCl or NaOH and the total volume was brought to 300 ml by adding deionized water. The variable amount of insoluble DAC was suspended with 100 mL deionized water. After adjusting pH to 2 with 6N HCl, insoluble DAC suspension was added into the polyamine solution at a speed of 10 ml/min with stirring at 500 RPM, followed by incubation for 60 minutes at 70° C. The particles were forced to pass through a mesh screen to achieve gel particles with a uniform size with different diameters. The particles suspension was titrated with 5M sodium hydroxide solution to adjust pH to 8.5. Deionized water was added to bring the total volume of gel particles suspension to 500 ml at pH 8.5. The gel particles suspension was incubated at 70° C. for an additional 60 minutes and the pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 for 60 minutes with stirring and precipitated by gravity at room temperature. After the supernatant was aspirated, the precipitated gel particles were washed with 4 liters deionized water twice and precipitated by gravity. The precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 14

Polysaccharide-polyamine copolymers in particle form were directly synthesized through titration of the insoluble DAC with alcohol. The 50 g branched polyamines including poly(allylamine) (MW 58K and 15K) or polyethyleneimine (MW 750K and 25K) were dissolved in deionized water to get 100 ml of total volume. The pH of the solution was adjusted to 9.0 with 37% HCl or NaOH and the total volume was brought to 300 ml by adding deionized water. The variable amount of insoluble DAC was suspended with 100 mL deionized water. After adjusting pH to 2 with 6N HCl, insoluble DAC suspension was added into the polyamine solution at a speed of 10 ml/min with stirring at 500 RPM, followed by incubation for 60 minutes at 70° C. The particles were forced to pass through a mesh screen to achieve gel particles with a uniform size with different diameters. The particles suspension was titrated with 5M sodium hydroxide solution to adjust pH to 8.5. Absolute alcohol was added to bring the total volume of particles suspension to 500 ml at pH 8.5. The gel particles suspension was incubated at 70° C. for an additional 60 minutes and the pH of the suspension was checked every 10 minutes and adjusted to 8.5 with 5M sodium hydroxide solution. The gel particles were precipitated by gravity at room temperature. After the supernatant was aspirated, the particles were incubated with 4 liters of 100 mM sodium bicarbonate solution at pH 8.5 for 60 minutes with stirring and precipitated by gravity at room temperature. After the supernatant was aspirated, the precipitated gel particles were washed with 4 liters deionized water twice and precipitated by gravity. The precipitated gel particles were reduced by adding 10 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 15

Polysaccharide-polyamine copolymers in hydrogel form were synthesized by reacting DAC with PLA (MW 58K). The ratio of DAC to PEI was 1:5. The condition of reaction was without alcohol. The poly(allylamine hydrochloride), 5 g, (MW 58K) was added into a 10 ml deionized water. The pH of PLA was adjusted to 1.0 with 37% HCl. The pH of 20 ml of DAC solution, containing 1 g of soluble DAC, was adjusted to 1.0 by adding 6×HCl. The solutions of PLA and solution of DAC were incubated on ice for 10 minutes. The solution containing 5 g of PLA and solution containing 1 g of DAC were mixed and incubated on ice for 10 minutes with stirring. The 20 ml 5M NaOH solution was quickly added into a PLA-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass through a mesh screen to achieve gel particles with a uniform size. Deionized water was added to bring the total volume of gel particles suspension to 200 ml. The gel particles suspension was incubated at 70° C. for an additional 60 minutes. The pH of the suspension was checked every 10 minutes and adjusted to 8.5 with 5M sodium hydroxide solution or 6N HCl. The gel particles were precipitated by gravity at room temperature. After the supernatant was aspirated, the particles were incubated with 1 liter of 100 mM sodium bicarbonate solution at pH 8.5 for 60 minutes with stirring and precipitated by gravity at room temperature. After the supernatant was aspirated, the precipitated gel particles were washed with 1 liter deionized water twice and precipitated by gravity. The precipitated gel particles were reduced by adding 2 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 16

Polysaccharide-polyamine copolymers in hydrogel form were synthesized by reacting DAC with PLA (MW 58K). The ratio of DAC to PEI was 1:10. The condition of reaction was without alcohol. The poly(allylamine hydrochloride), 5 g, (MW 58K) was added into a 10 ml deionized water. The pH of PLA was adjusted to 1.0 with 37% HCl. The pH of 20 ml of DAC solution, containing 0.5 g of soluble DAC, was adjusted to 1.0 by adding 6×HCl. The solutions of PLA and solution of DAC were incubated on ice for 10 minutes. The solution containing 5 g of PLA and solution containing 0.5 g of DAC were mixed and incubated on ice for 10 minutes with stirring. The 20 ml 5M NaOH solution was quickly added into a PLA-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass through a mesh screen to achieve gel particles with a uniform size. Deionized water was added to bring the total volume of gel particles suspension to 200 ml. The gel particles suspension was incubated at 70° C. for an additional 60 minutes. The pH of the suspension was checked every 10 minutes and adjusted to 8.5 with 5M sodium hydroxide solution or 6N HCl. The gel particles were precipitated by gravity at room temperature. After the supernatant was aspirated, the particles were incubated with 1 liter of 100 mM sodium bicarbonate solution at pH 8.5 for 60 minutes with stirring and precipitated by gravity at room temperature. After the supernatant was aspirated, the precipitated gel particles were washed with 1 liter deionized water twice and precipitated by gravity. The precipitated gel particles were reduced by adding 2 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 17

Polysaccharide-polyamine copolymers in hydrogel form were synthesized by reacting DAC with PLA (MW 58K). The ratio of DAC to PEI was 1:20. The condition of reaction was without alcohol. The poly(allylamine hydrochloride), 5 g, (MW 58K) was added into a 10 ml deionized water. The pH of PLA was adjusted to 1.0 with 37% HCl. The pH of 20 ml of DAC solution, containing 0.25 g of soluble DAC, was adjusted to 1.0 by adding 6×HCl. The solutions of PLA and solution of DAC were incubated on ice for 10 minutes. The solution containing 5 g of PLA and solution containing 0.25 g of DAC were mixed and incubated on ice for 10 minutes with stirring. The 20 ml 5M NaOH solution was quickly added into a PLA-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass through a mesh screen to achieve gel particles with a uniform size. Deionized water was added to bring the total volume of gel particles suspension to 200 ml. The gel particles suspension was incubated at 70° C. for an additional 60 minutes. The pH of the suspension was checked every 10 minutes and adjusted to 8.5 with 5M sodium hydroxide solution or 6N HCl. The gel particles were precipitated by gravity at room temperature. After the supernatant was aspirated, the particles were incubated with 1 liter of 100 mM sodium bicarbonate solution at pH 8.5 for 60 minutes with stirring and precipitated by gravity at room temperature. After the supernatant was aspirated, the precipitated gel particles were washed with 1 liter deionized water twice and precipitated by gravity. The precipitated gel particles were reduced by adding 2 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 18

Polysaccharide-polyamine copolymers in hydrogel form were synthesized by reacting DAC with PLA (MW 58K). The ratio of DAC to PEI was 1:5. The condition of reaction was without alcohol. The poly(allylamine hydrochloride), 5 g, (MW 58K) was added into a 10 ml deionized water. The pH of PLA was adjusted to 1.0 with 37% HCl. The pH of 20 ml of DAC solution, containing 1 g of soluble DAC, was adjusted to 1.0 by adding 6×HCl. The solutions of PLA and solution of DAC were incubated on ice for 10 minutes. The solution containing 5 g of PLA and solution containing 1 g of DAC were mixed and incubated on ice for 10 minutes with stirring. The 20 ml 5M NaOH solution was quickly added into a PLA-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass through a mesh screen to achieve gel particles with a uniform size. Absolute alcohol was added to bring the total volume of gel particles suspension to 200 ml. The gel particles suspension was incubated at 70° C. for an additional 60 minutes. The pH of the suspension was checked every 10 minutes and adjusted to 8.5 with 5M sodium hydroxide solution or 6N HCl. The gel particles were precipitated by gravity at room temperature. After the supernatant was aspirated, the particles were incubated with 1 liter of 100 mM sodium bicarbonate solution at pH 8.5 for 60 minutes with stirring and precipitated by gravity at room temperature. After the supernatant was aspirated, the precipitated gel particles were washed with 1 liter deionized water twice and precipitated by gravity. The precipitated gel particles were reduced by adding 2 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 19

Polysaccharide-polyamine copolymers in hydrogel form were synthesized by reacting DAC with PLA (MW 58K). The ratio of DAC to PEI was 1:10. The condition of reaction was without alcohol. The poly(allylamine hydrochloride), 5 g, (MW 58K) was added into a 10 ml deionized water. The pH of PLA was adjusted to 1.0 with 37% HCl. The pH of 20 ml of DAC solution, containing 0.5 g of soluble DAC, was adjusted to 1.0 by adding 6×HCl. The solutions of PLA and solution of DAC were incubated on ice for 10 minutes. The solution containing 5 g of PLA and solution containing 0.5 g of DAC were mixed and incubated on ice for 10 minutes with stirring. The 20 ml 5M NaOH solution was quickly added into a PLA-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass mesh screen to achieve gel particles with a uniform size. Absolute alcohol was added to bring the total volume of gel particles suspension to 200 ml. The gel particles suspension was incubated at 70° C. for an additional 60 minutes. The pH of the suspension was checked every 10 minutes and adjusted to 8.5 with 5M sodium hydroxide solution or 6N HCl. The gel particles were precipitated by gravity at room temperature. After the supernatant was aspirated, the particles were incubated with 1 liter of 100 mM sodium bicarbonate solution at pH 8.5 for 60 minutes with stirring and precipitated by gravity at room temperature. After the supernatant was aspirated, the precipitated gel particles were washed with 1 liter deionized water for two times and precipitated by gravity. The precipitated gel particles were reduced by adding 2 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 20

Polysaccharide-polyamine copolymers in hydrogel form were synthesized by reacting DAC with PLA (MW 58K). The ratio of DAC to PEI was 1:20. The condition of reaction was without alcohol. The poly(allylamine hydrochloride), 5 g, (MW 58K) was added into a 10 ml deionized water. The pH of PLA was adjusted to 1.0 with 37% HCl. The pH of 20 ml of DAC solution, containing 0.25 g of soluble DAC, was adjusted to 1.0 by adding 6×HCl. The solutions of PLA and solution of DAC were incubated on ice for 10 minutes. The solution containing 5 g of PLA and solution containing 0.25 g of DAC were mixed and incubated on ice for 10 minutes with stirring. The 20 ml 5M NaOH solution was quickly added into a PLA-DAC mixture and incubated on ice with stirring at 1000 RPM for 5 minutes. The mixture was kept on ice without agitation until the hydrogel was completely formed. The hydrogel was incubated at 70° C. for 60 minutes. The hydrogel was forced to pass mesh screen to achieve gel particles with a uniform size. Absolute alcohol was added to bring the total volume of gel particles suspension to 200 ml. The gel particles suspension was incubated at 70° C. for an additional 60 minutes. The pH of the suspension was checked every 10 minutes and adjusted to 8.5 with 5M sodium hydroxide solution or 6N HCl. The gel particles were precipitated by gravity at room temperature. After the supernatant was aspirated, the particles were incubated with 1 liter of 100 mM sodium bicarbonate solution at pH 8.5 for 60 minutes with stirring and precipitated by gravity at room temperature. After the supernatant was aspirated, the precipitated gel particles were washed with 1 liter deionized water twice and precipitated by gravity. The precipitated gel particles were reduced by adding 2 g sodium borohydride and incubated at room temperature for 72 hours. The reduced gel particles were washed with deionized water to remove the excessive sodium borohydride and PEI until the pH of the solution was between 5 and 6. The washed gel particles were freeze dried (optional).

Example 21

An in vitro phosphate binding capacity assay (in vitro test example) was prepared. A standard phosphate solution (200 mM) was made from phosphoric acid (13.7 ml; 85%), sodium carbonate (3.18 g), sodium chloride (4.68 g), and deionized water (1 L). The solution was adjusted to pH 7 with 1 M NaOH. A diluent solution was made similarly without the phosphate, and it was adjusted to pH 7 with acetic acid. Appropriate aliquots of the phosphate solution and diluent were mixed to obtain test solutions with starting phosphate concentrations in the range from 100 mM-10 mM.

Polysaccharide-polyamine copolymers (Cellulose-PEI 750K DAC:PEI 1:20) (10 mg) were suspended in the standard phosphate solution (5 mL), and the mixture was adjusted to the appropriate pH with 6M HCl or 6M NaOH. The mixture was stirred for 1 hour at 37° C. and adjusted again to the appropriate pH. The solid copolymers were pelleted by centrifugation at 14,000×g for 30 minutes at 37° C. and the supernatant analyzed for phosphate. Phosphate concentrations were determined spectrophotometrically using a standard molybdate assay. Bound phosphate is determined by the following equation: Bound Phosphate (mmol/g)=[(orignal phosphate concentration-unbound phosphate concentration).times.Vol.times.1000]/MassP; wherein Vol.=volume of test solution (L); MassP=LOD adjusted mass of polymer (mg).

Example 22

A further example was prepared to examine the effect of polysaccharide-polyamine copolymers on dietary phosphorus excretion in a rat model. Female and Male Sprague-Dawley rats, approximately 6 weeks old from Harlan Laboratories were used in these studies. Animals are singly housed in normal cages and fed the standard diet, rodent 5008 Fomulab diet (LabDiet, Louis, Mo.) containing 1.07% inorganic phosphorus and tap water. The polysaccharide-polyamine copolymers and cellulose control are mixed into a powdered diet to achieve final concentrations of test article (w/w). The rats are housed in normal cage and fed with the standard diet for seven days prior to experimental use. Experimental samples were prepared by adding 1% by weight polysaccharide-polyamine copolymers (Cellulose-PEI 750K DAC:PEI 1:20) to the feed while control samples were prepared by adding 1% by weight cellulose to the feed for other rats. As shown below, "CelloPhos" refers to the experimental samples having the polysaccharide-polyamine copolymers.

Each rat is continually fed with standard diet for additional seven days. To establish baseline of 24-hour phosphorous excretion, the rats are placed in metabolic cages for 24 hours on day 15. Their 24-hour urine is collected and its phosphorus content measured spectrophotometrically by a standard molybdate assay to determine total amount of 24-hour urinary phosphorus excretion in mg/day. Blood samples were collected for serum chemistry analysis on day 15. Any rats with outlying values are excluded; and the remainder of the rats are distributed into groups.

Next, the standard diet is replaced with experimental diet vs. negative control diet. On days 23 and 38, 24-hour urine samples from the rats are collected. Blood samples were collected for serum chemistry analysis on day 38. The phosphorous concentration of all samples are measured spectrophotometrically by a standard molybdate assay. Percentage reduction of urinary phosphorous is determined by the following equation:

% Reduction of Urinary Phosphorous=[(24-hour urinary phosphorous excretion baseline (mg/day)−urinary phosphorous of experimental (mg/day))/24-hour urinary phosphorous excretion baseline (mg/day)]×100.

Experimental Study Design

TABLE 2

| | Group of Animal | |
|---|---|---|
| Gender of Animal | Cellulose 1% | Experimental (CelloPhos) 1% |
| Female | 3 | 3 |
| Male | 3 | 3 |

Experimental Study Schedule

TABLE 3

| Schedule | Comments |
|---|---|
| Throughout the whole experimental period | Weigh animals every 3 days<br>Weigh animal diet and calculate total amount of consumed diet every 3 days |
| Day 1-7 | Receive animals, quarantine and adaptation (7 days). Animals fed with the standard diet. |
| Day 8-14 | Animals are fed with the standard diet for additional 7 days. |
| Day 15 Blood Sample | Collect serum for serum chemistry analysis |
| Day 15 Urinary Sample | Collect 24 hour urine |

TABLE 3-continued

| Schedule | Comments |
|---|---|
| Day 16-22 | Treat with different experimental diets (containing copolymers or controls). |
| Day 23 (Week 1) Urinary Sample | Collect 24 hour urine on Day 23 |
| Day 24-37 | Treat with different experimental diets (containing copolymers or controls). |
| Day 38 Blood Sample | Collect serum for serum chemistry analysis |
| Day 38 Urinary Sample | Collect 24 hour urine (The detailed method for collecting urine sample is described below). |

TABLE 4

Decrease in total daily urinary phosphorus

| | Experimental (Cellophos) (1%) Day 7 | Experimental (CelloPhos) (1%) Day 21 | Negative Control (1% Cellulose) Day 7 | Negative Control (1% Cellulose) Day 21 |
|---|---|---|---|---|
| Percent of Reduction of Urinary Phosphorus | 43.8 ± 5.2 | 57.0 ± 2.8 | 3.1 ± 3.8 | 0 ± 1.3 |

Animals administered experimental diet containing 1% polysaccharide-polyamine copolymers for seven days had a 43.8±5.2% decrease in total 24-hour urinary phosphorus, while animals administered for 21 days had 57.0±2.8% decreases in total urinary phosphorus, respectively. But animals administered the negative control diet containing 1% cellulose had less 7% decrease.

All animals increased of their weight throughout the whole experimental period. This data indirectly indicates that oral administration of 1% polysaccharide-polyamine copolymers has no any significant adverse effect on the gastrointestinal (GI) tract of tested animals.

Orally administrated polysaccharide-polyamine copolymers is able to significantly reduce 24-hour total amount of urinary phosphorous excretion through blocking absorption of dietary phosphorus from GI tract.

There is no obvious toxic effect or organ damage caused by orally administrated CelloPhos at 1% (W/W) concentration.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of Applicants' contribution. The actual scope of the protection sought is intended to be defined in the following claims when viewed in their proper perspective based on the prior art.

What is claimed is:

1. A polysaccharide-polyamine copolymer having an amino functionality which will provide a protonatable copolymeric material having a three-dimensional structure with cationic sites through protonation, the polysaccharide-polyamine copolymer comprising:
   a selectively oxidized polysaccharide having a 2,3-dialdehyde moiety; and
   amino polymers which provide an amino functionality, the amino polymers cross linking the oxidized polysaccharides to provide a particulate polysaccharide-polyamine copolymer having an amino functionality which when protonated will provide the cationic copolymeric material with a nitrogen content of at least 12.3 wt. %, both the polysaccharide-polyamine copolymer and cationic copolymeric material being water insoluble, wherein the amino polymers are in a branched or dendritic form.

2. The polysaccharide-polyamine copolymer of claim 1, wherein the amino polymers have a nitrogen content of at least 24.5 wt. %, based on the weight of the amino polymers and a molecular weight in the range of from about 15,000 to about 900,000.

3. The polysaccharide-polyamine copolymer of claim 1, wherein the selectively oxidized polysaccharide are selected from the group consisting of selectively oxidized cellulose, selectively oxidized starch, selectively oxidized amylose, selectively oxidized chitosan, selectively oxidized dextran, selectively oxidized glycogen, selectively oxidized chitin and mixtures thereof, the polysaccharide having been oxidized in an amount effective to provide the 2,3-dialdehyde moiety which is reactive with the amino polymers.

4. The polysaccharide-polyamine copolymer of claim 1, wherein the selectively oxidized polysaccharide have β-1,4-glycosidic bonds or β-1,6-glycosidic bonds.

5. The polysaccharide-polyamine copolymer of claim 1, wherein the selectively oxidized polysaccharide have β-1,4-glycosidic bonds.

6. The polysaccharide-polyamine copolymer of claim 1, wherein the selectively oxidized polysaccharide is selected from the group consisting of selectively oxidized cellulose, selectively oxidized chitosan, selectively oxidized chitin, selectively oxidized amylose and mixtures thereof.

7. The polysaccharide-polyamine copolymer of claim 1, wherein the amino polymers which provide a cationic amino functionality are selected from the group consisting of polyethylenimine, poly(allylamine) and polypropylenimine tetramine and mixtures thereof.

8. The polysaccharide-polyamine copolymers of claim 1, wherein the particulates of the polysaccharide-polyamine copolymer and cationic copolymeric material have sizes in the range of from about 100 μm to about 10 mm.

9. The polysaccharide-polyamine copolymer of claim 1, wherein the particulate polysaccharide-polyamine copolymer and cationic copolymeric material has particulates having sizes in the range of from about 100 μm to about 10 mm and pore sizes of less than about 50 μm.

10. A method of making the polysaccharide-polyamine copolymer and copolymeric materials which when protonated have cationic sites of claim 1, the method comprising:

reacting selectively oxidized polysaccharides having a 2,3 di-aldehyde moieties with amino polymers, the reaction providing a particulate polysaccharide-polyamine copolymer and copolymeric material having an amino functionality in an amount which when protonated provides a cationic copolymeric material with a nitrogen content of at least 12.3 wt. %, based upon the weight of the cationic copolymeric material, both the polysaccharide-polyamine copolymer and copolymeric material being water insoluble.

11. The method claim 10, wherein the selectively oxidized polysaccharides are selected from the group consisting of consisting of selectively oxidized cellulose, selectively oxidized starch, selectively oxidized amylose, selectively oxidized chitosan, selectively oxidized dextran, selectively oxidized glycogen, selectively oxidized chitin and mixtures thereof, the polysaccharide having been oxidized in an amount effective to provide the 2,3 di-aldehyde moiety which is reactive with the amino polymers.

12. The method of claim 10, wherein the amino polymers have a nitrogen content of at least 24.5 wt. %, based on the weight of the amino polymers, and a molecular weight in the range of from about 15,000 to about 900,000.

13. The method of claim 10, wherein the amino polymers which provide a cationic amino functionality are selected from the group consisting of polyethylenimine, poly(allylamine) and polypropylenimine tetramine and mixtures thereof.

14. The method of claim 10, wherein the selectively oxidized polysaccharides have β-1,4-glycosidic bonds.

15. The method of claim 10, wherein the selectively oxidized polysaccharides have β-1,6-glycosidic bonds.

16. The method of claim 10, wherein the selectively oxidized polysaccharides is selected from the group consisting of selectively oxidized cellulose, selectively oxidized chitosan, selectively oxidized chitin, selectively oxidized amylose and mixtures thereof.

17. The method of claim 10, wherein the particulate polysaccharide-polyamine copolymer and copolymeric material has particulates having sizes in the range of from about 100 μm to about 10 mm and pore sizes of less than about 50 μm.

* * * * *